United States Patent
Seto et al.

(10) Patent No.: US 9,603,617 B2
(45) Date of Patent: Mar. 28, 2017

(54) MEDICAL APPARATUS

(71) Applicant: Seiko Epson Corporation, Tokyo (JP)

(72) Inventors: Takeshi Seto, Chofu (JP); Kazuaki Uchida, Fujimi-machi (JP); Hideki Kojima, Matsumoto (JP); Hirokazu Sekino, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 311 days.

(21) Appl. No.: 13/895,129

(22) Filed: May 15, 2013

(65) Prior Publication Data

US 2013/0310862 A1    Nov. 21, 2013

(30) Foreign Application Priority Data

| May 15, 2012 | (JP) | 2012-111570 |
| Jun. 26, 2012 | (JP) | 2012-142742 |
| Jun. 26, 2012 | (JP) | 2012-142743 |

(51) Int. Cl.
  *A61B 17/3203*  (2006.01)
  *A61B 17/00*   (2006.01)

(52) U.S. Cl.
  CPC .... *A61B 17/3203* (2013.01); *A61B 17/32037* (2013.01); *A61B 2017/00075* (2013.01); *A61B 2017/00154* (2013.01); *A61B 2017/00194* (2013.01); *A61B 2017/32032* (2013.01)

(58) Field of Classification Search
  CPC .......... A61B 17/3203; A61B 17/32037; A61B 2017/32032; A61B 19/5212; A61B 2019/5227; B26F 2003/006; A61M 37/0092

USPC .............................. 606/167–170; 83/53, 177
See application file for complete search history.

(56) References Cited

U.S. PATENT DOCUMENTS

| 6,086,544 A * | 7/2000 | Hibner et al. ................. 600/568 |
| 7,901,374 B2 | 3/2011 | Seto et al. |
| 2001/0039389 A1 * | 11/2001 | Sakurai et al. .................... 601/2 |
| 2002/0049375 A1 * | 4/2002 | Strommer et al. ............. 600/407 |
| 2007/0198004 A1 | 8/2007 | Altshuler et al. |
| 2008/0309705 A1 * | 12/2008 | Ito ................................... 347/19 |
| 2010/0082053 A1 * | 4/2010 | Hama et al. ................... 606/167 |
| 2011/0037795 A1 * | 2/2011 | Kojima et al. ................... 347/10 |
| 2011/0054505 A1 * | 3/2011 | Kojima et al. ................ 606/167 |
| 2012/0108900 A1 * | 5/2012 | Viola et al. .................... 600/109 |
| 2012/0176431 A1 | 7/2012 | Kojima |

FOREIGN PATENT DOCUMENTS

| CN | 102348425 A | 2/2012 |
| JP | 2008-082202 A | 4/2008 |
| JP | 2010-051896 A | 3/2010 |
| JP | 2012-143374 A | 8/2012 |

* cited by examiner

*Primary Examiner* — David C Eastwood
*Assistant Examiner* — Mikail Mannan
(74) *Attorney, Agent, or Firm* — Maschoff Brennan

(57) ABSTRACT

Liquid is ejected in a pulse-like manner from a nozzle provided at the distal end of a liquid ejection pipe. When the liquid is ejected, moving speed of the nozzle is detected. A driving frequency of a piezoelectric element is increased when the moving speed increase. The driving frequency is reduced when the moving speed decreases. Consequently, it is possible to prevent the number of times the liquid is ejected per unit length from changing according to the moving speed of the nozzle. Therefore, it is possible to excise a biological tissue at stable excision depth.

13 Claims, 28 Drawing Sheets

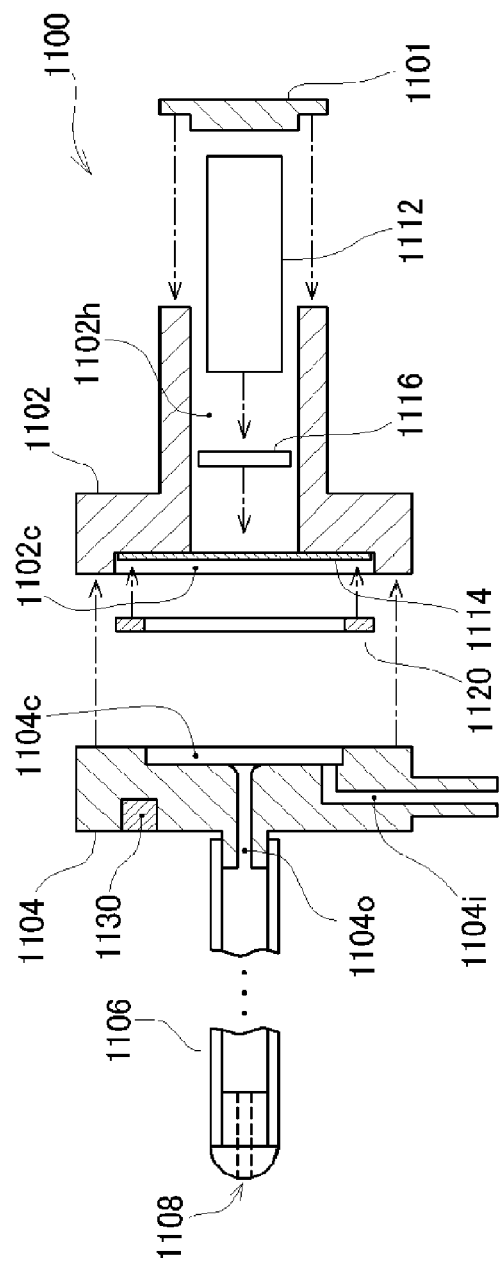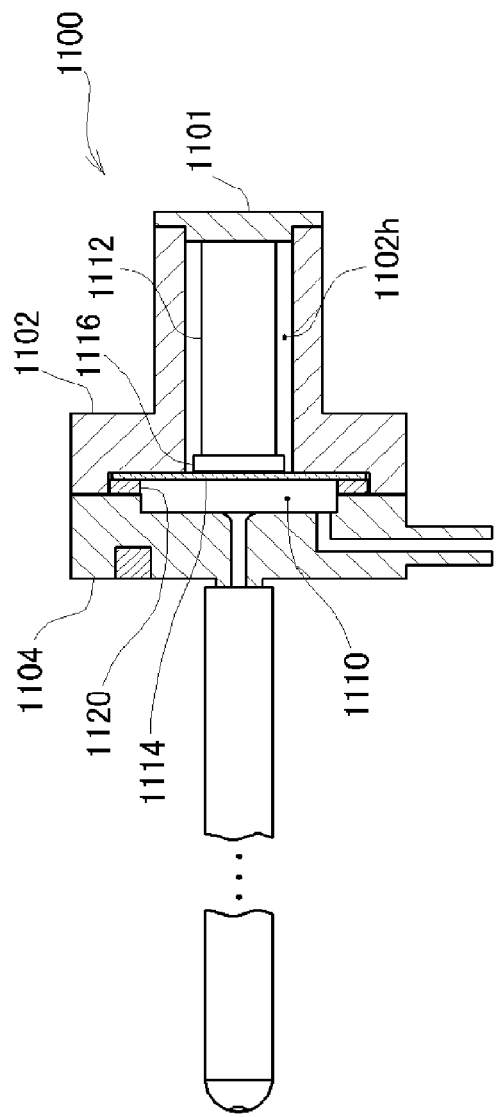
FIG. 2A
FIG. 2B

| MOVING SPEED OF NOZZLE | DRIVING FREQUENCY (Hz) | NUMBER OF PULSES PER UNIT LENGTH |
|---|---|---|
| 0.01 | 10 | 1000 |
| 0.2 | 200 | 1000 |
| 0.4 | 400 | 1000 |
| 0.6 | 600 | 1000 |
| 0.8 | 800 | 1000 |
| 1.0 | 1000 | 1000 |

| DRIVING FREQUENCY (Hz) | SUPPLY FLOW RATE |
|---|---|
| 0 | 1 |
| 200 | 1 |
| 400 | 2 |
| 600 | 3 |
| 800 | 4 |
| 1000 | 5 |
| 1200 | 5 |

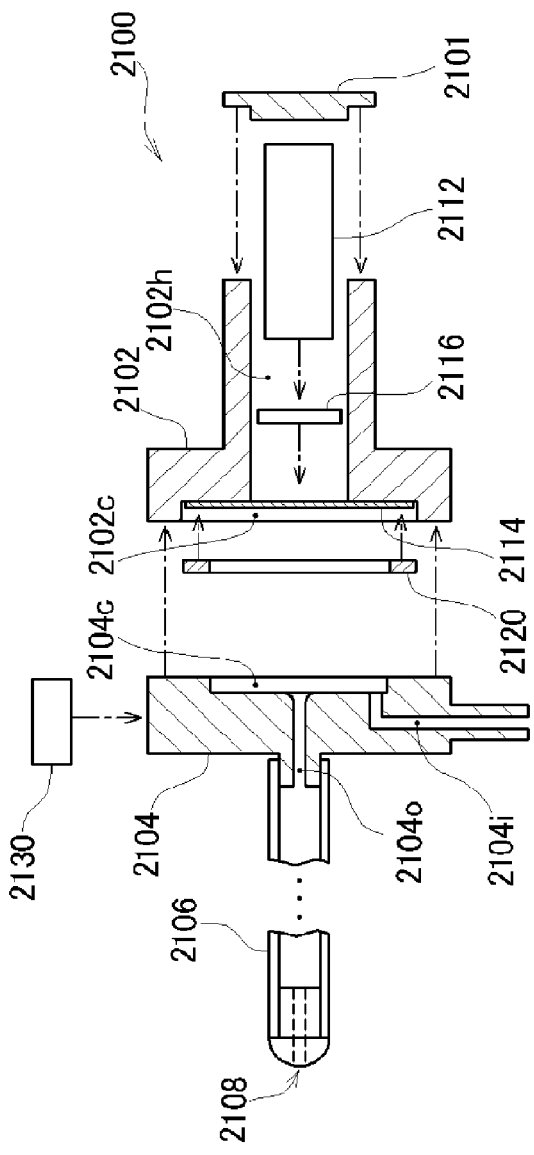
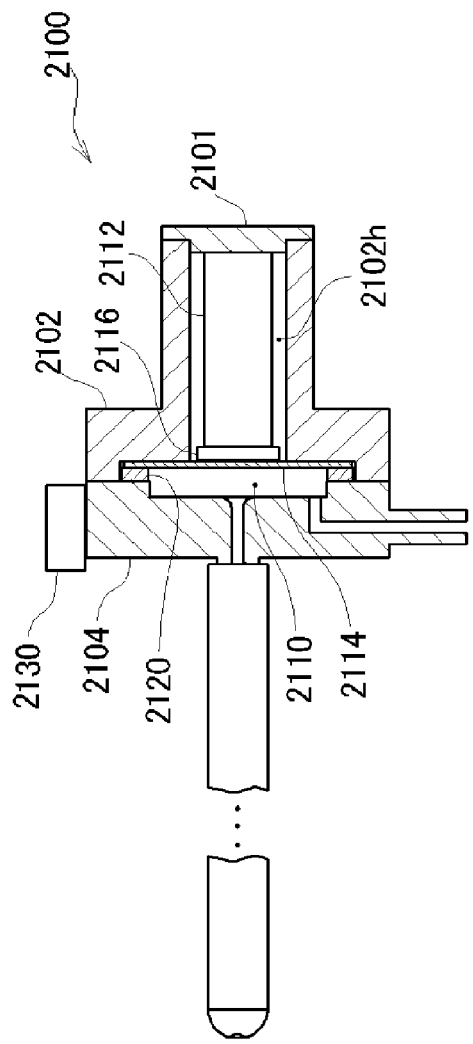
FIG.13A
FIG.13B

| MOVING SPEED OF NOZZLE | DRIVING FREQUENCY (Hz) | NUMBER OF PULSES PER UNIT LENGTH |
|---|---|---|
| 0.01 | 10 | 1000 |
| 0.2 | 200 | 1000 |
| 0.4 | 400 | 1000 |
| 0.6 | 600 | 1000 |
| 0.8 | 800 | 1000 |
| 1.0~ | 1000 | 1000 |

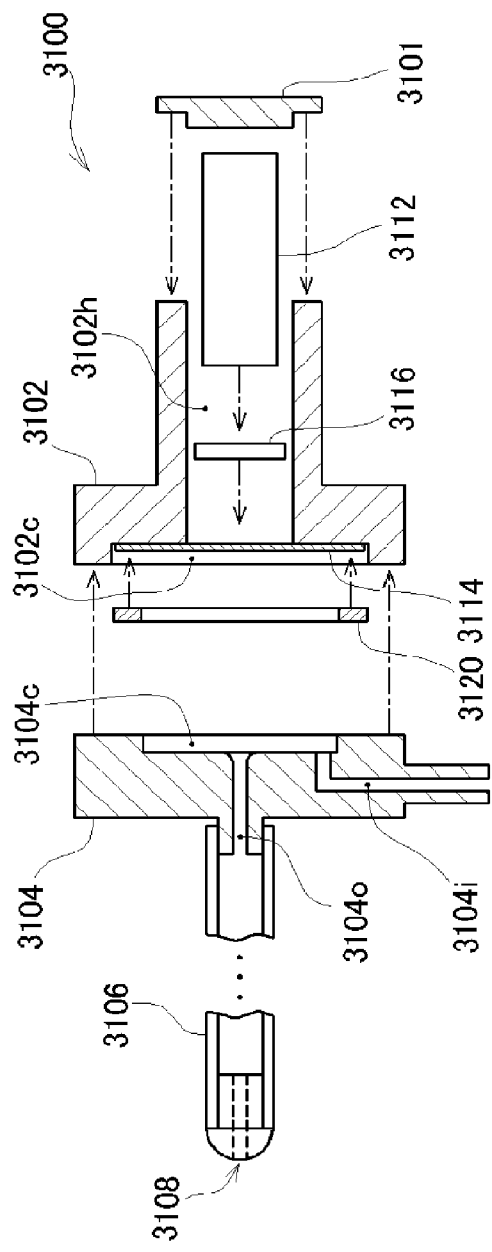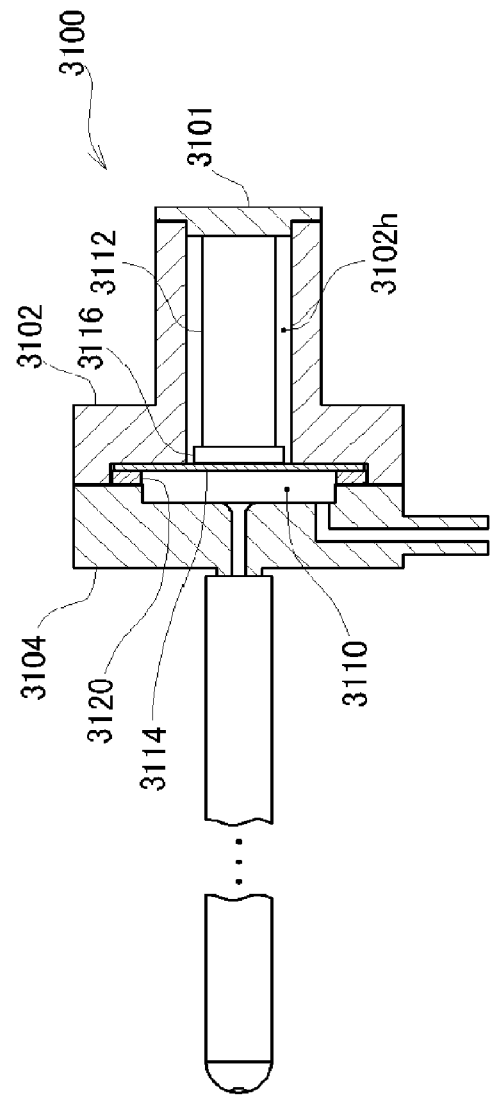
FIG. 22A
FIG. 22B

| MOVING SPEED OF NOZZLE | DRIVING FREQUENCY (Hz) | NUMBER OF PULSES PER UNIT LENGTH |
|---|---|---|
| 0.01 | 10 | 1000 |
| 0.2 | 200 | 1000 |
| 0.4 | 400 | 1000 |
| 0.6 | 600 | 1000 |
| 0.8 | 800 | 1000 |
| 1.0 ~ | 1000 | 1000 |

FIG.27

MEDICAL APPARATUS

CROSS-REFERENCE TO RELATED APPLICATION

The present application claims priority from Japanese applications P2012-111570A filed on May 15, 2012, P2012-142742 filed on Jun. 26, 2012, and P2012-142743 filed on Jun. 26, 2012, the contents of which are hereby incorporated by reference into this application.

BACKGROUND

1. Technical Field

The present invention relates to a medical apparatus.

2. Related Art

There is known a medical apparatus that ejects pressurized liquid to cut a biological tissue. For example, JP-A-2008-82202 discloses a medical apparatus that ejects pressurized liquid from a nozzle to a biological tissue in a pulse-like manner to thereby incise or excise the biological tissue. JP-A-2010-51896 discloses a medical apparatus that detects the tilt of a nozzle to thereby adjust a flow rate of a liquid feed pump.

However, in the medical apparatuses disclosed in both the patent literatures, since the number of times of ejection per unit length of the biological tissue changes when speed for moving the tip of the nozzle (moving speed) is different, depth of excision of the biological tissue (excision depth) changes. Therefore, it is difficult to excise the biological tissue at stable depth.

SUMMARY

An advantage of some aspects of the invention is to provide a medical apparatus capable of excising a biological tissue at stable depth even if the moving speed of the tip of a nozzle changes.

An aspect of the invention is directed to a medical apparatus that ejects liquid from a nozzle provided at the distal end of a liquid ejection pipe. The medical apparatus includes: a pulsation generating unit configured to change the capacity of a liquid chamber connected to the liquid ejection pipe according to displacement of a piezoelectric element and generate pulsation in the liquid; a liquid supplying unit configured to supply the liquid to the liquid chamber; a moving-speed detecting unit configured to detect the moving speed of the nozzle; and a pulsation-generation control unit configured to set a driving frequency of the piezoelectric element higher when the moving speed of the nozzle is second moving speed higher than first moving speed than when the moving speed of the nozzle is the first moving speed and control the pulsation.

If the liquid is ejected at the same driving frequency irrespective of the moving speed of the nozzle, since the number of times the liquid is ejected per unit length changes according to the moving speed of the nozzle, excision depth also changes. Therefore, if the driving frequency of the piezoelectric element is set higher when the moving speed of the nozzle is the second moving speed higher than the first moving speed than when the moving speed of the nozzle is the first moving speed and the pulsation is controlled, it is possible to excise a biological tissue at stable excision depth irrespective of the moving speed of the nozzle.

In the medical apparatus, the pulsation-generation control unit may perform the pulsation control by increasing the driving frequency of the piezoelectric element when the moving speed of the nozzle increases or reducing the driving frequency of the piezoelectric element when the moving speed of the nozzle decreases.

Alternatively, the medical apparatus may further include: a liquid ejecting unit including the liquid ejection pipe erected therefrom and the liquid chamber formed on the inside thereof; a photographing unit attached to the liquid ejecting unit and configured to photograph target images, which are images of a place where the liquid is ejected, at a predetermined time interval; and a moving-distance detecting unit configured to compare the target images obtained at the predetermined time interval to thereby detect, on the target images, a moving distance of the place where the liquid is ejected. The moving-speed detecting unit may detect the moving speed of the nozzle on the basis of the moving distance.

The medial apparatus may further include: a liquid ejecting unit including the liquid ejection pipe erected therefrom and the liquid chamber formed on the inside thereof; a photographing unit configured to photograph the liquid ejecting unit from at least two directions at a predetermined time interval; and a mark member attached to a predetermined position of the liquid ejecting unit or the liquid ejection pipe. The moving-speed detecting unit may detect the moving speed of the nozzle by detecting the position of the mark member out of an image photographed by the photographing unit.

Alternatively, in the medical apparatus, the mark member may be attached to a plurality of places of the liquid ejecting unit or the liquid ejection pipe. The moving-speed detecting unit may be a unit configured to detect the direction of the nozzle on the basis of the positions of a plurality of the mark members and detect the moving speed of the nozzle taking into account the direction of the nozzle as well.

Not all of a plurality of elements in the aspects of the invention are essential. In order to solve a part or all of the problems or in order to attain a part or all of effects described in this specification, concerning a part of the plurality of elements, it is possible to perform a change, deletion, replacement with new other elements, and partial deletion of limitation contents. In order to solve a part or all of the problems or in order to attain a part or all of the effects described in this specification, it is also possible to combine a part or all of technical features included in the aspects of the invention with a part or all of technical features of other aspects of the invention to obtain an independent aspect of the invention.

BRIEF DESCRIPTION OF THE DRAWINGS

The invention will be described with reference to the accompanying drawings, wherein like numbers reference like elements.

FIGS. 2A and 2B are explanatory diagrams showing detailed structure of an applicator in the first embodiment.

FIGS. 13A and 13B are explanatory diagrams showing detailed structure of an applicator in the second embodiment.

FIGS. 22A and 22B are explanatory diagrams showing detailed structure of an applicator in the third embodiment.

FIG. 27 is an explanatory diagram conceptually showing a table in which driving frequencies corresponding to moving speeds of the nozzle are stored in the third embodiment.

DESCRIPTION OF EXEMPLARY EMBODIMENTS

A. First Embodiment
A-1. Apparatus Configuration

Figure 1:
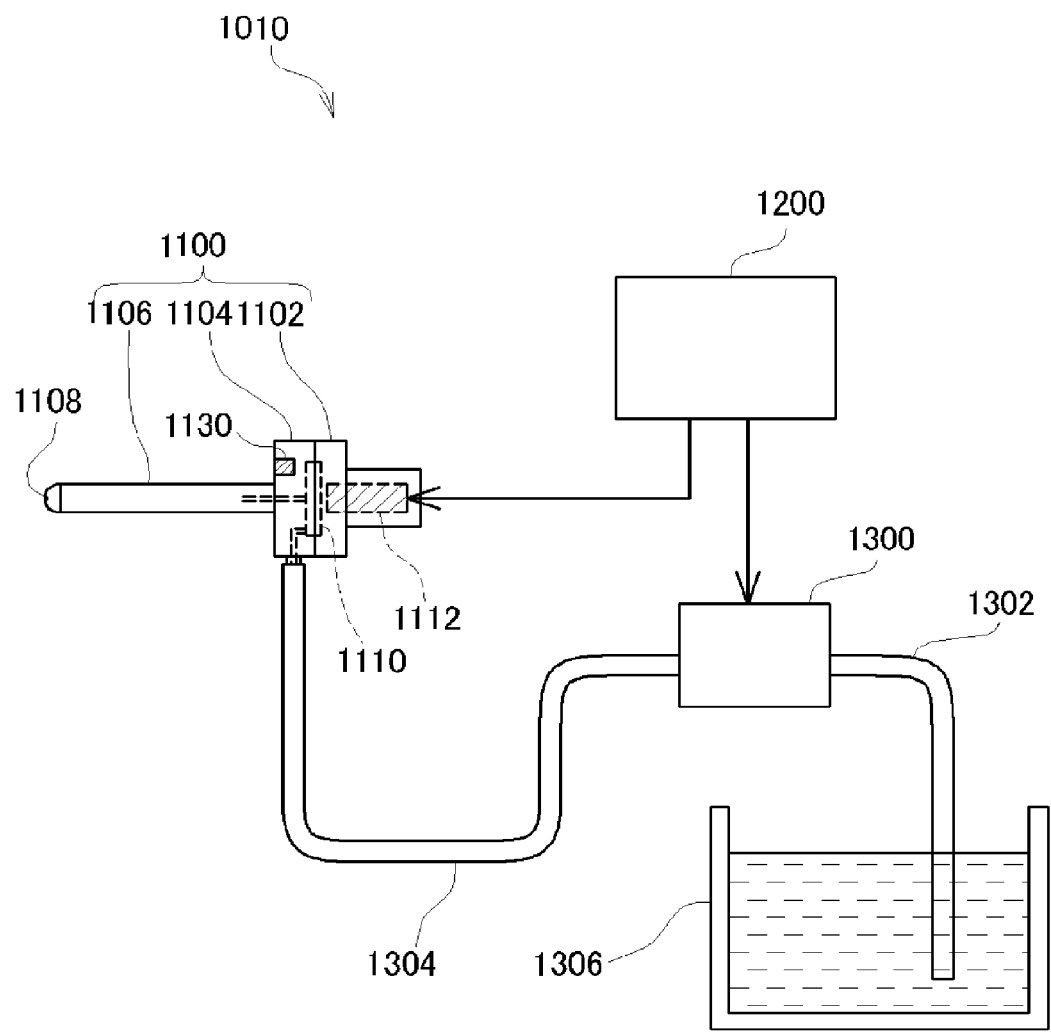
FIG. 1 is an explanatory diagram showing a rough configuration of a medical apparatus in a first embodiment.

FIG. 1 is an explanatory diagram showing a rough configuration of a medical apparatus 1010 in a first embodiment. The medical apparatus 1010 shown in the figure is used for a surgical operation method for incising or excising a biological tissue by ejecting liquid such as water or saline to the biological tissue.

As shown in the figure, the medical apparatus 1010 in the first embodiment includes an applicator 1100 held by an operator by hand and operated to eject liquid, a liquid supply unit 1300 configured to supply the liquid to the applicator 1100, a liquid container 1306 configured to store the liquid to be ejected, and a control unit 1200 configured to control the operation of the applicator 1100 and the liquid supply unit 1300.

The applicator 1100 includes a first case 1102, a second case 1104 attached to the first case 1102, a liquid ejection pipe 1106 provided to project from the second case 1104 to the opposite side of the first case 1102, and a nozzle 1108 provided at the distal end of the liquid ejection pipe 1106. A liquid chamber 1110 is formed on a mating face of the first case 1102 and the second case 1104. A laminated piezoelectric element 1112 is housed in the first case 1102. When a voltage is applied to the piezoelectric element 1112 to expand the piezoelectric element 1112, the liquid chamber 1110 is deformed and the capacity of the liquid chamber 1110 decreases. When the voltage applied to the piezoelectric element 1112 is released, the liquid chamber 1110 is restored from the deformation and the capacity of the liquid chamber 1110 returns to the original capacity. When the application of the voltage to the piezoelectric element 1112 and the release of the applied voltage (hereinafter also referred to as on and off) are repeated at a predetermined frequency, the capacity of the liquid chamber 1110 repeats an increase and a decrease according to the voltage application and the release. Pulsation occurs in the pressure on the inside of the liquid chamber 1110. The piezoelectric element 1112 in the first embodiment functions as the "pulsation generating unit" in the invention.

A liquid supply unit 1300 is connected to the liquid chamber 1110 via a second connection tube 1304. The liquid supply unit 1300 is connected to the liquid container 1306 via a first connection tube 1302. When the liquid supply unit 1300 is actuated, the liquid in the liquid container 1306 is supplied to the liquid chamber 1110. When a driving voltage turned on and off at a predetermined frequency is applied to the piezoelectric element 1112 while the liquid supply unit 1300 is actuated to supply the liquid to the liquid chamber 1110, the capacity of the liquid chamber 1110 repeats an increase and a decrease. Pulse-like ejection from the nozzle 1108 is caused according to the pulsation of the pressure in the liquid chamber 1110. The pulse-like ejection of the liquid from the nozzle 1108 is continued in a period in which the driving voltage is applied.

An acceleration sensor 1130 is also provided in the applicator 1100. An output of the acceleration sensor 1130 is input to the control unit 1200 via a not-shown cable. The control unit 1200 detects the moving speed of the nozzle 1108 on the basis of the acceleration of the applicator 1100 detected by the acceleration sensor 1130. As explained in detail below, the control unit 1200 controls, according to the moving speed of the nozzle 1108, the number of times the driving voltage is applied to the piezoelectric element 112 per unit time (a driving frequency) and a flow rate of the liquid supplied to the liquid chamber 1110 by the liquid supply unit 1300 (a supply flow rate). The control unit 1200 in the first embodiment corresponds to the "pulsation-generation control unit" in the invention. The acceleration sensor 1130 in the first embodiment corresponds to the "moving-speed detecting unit" in the invention.

FIGS. 2A and 2B are explanatory diagrams showing detailed structure of the applicator 1100. An exploded sectional view of the applicator 1100 is shown in FIG. 2A. A sectional view after assembly is shown in FIG. 2B. In the first case 1102, a large circular shallow recess 1102c is formed substantially in the center of a face mating with the second case 1104. A through-hole 1102h circular in section is formed in the center position of the recess 1102c to pierce through the first case 1102.

A thin diaphragm 1114 of metal is provided in the bottom of the recess 1102c to close the through-hole 1102h. The peripheral edge portion of the diaphragm 1114 is hermetically fixedly attached to the bottom of the recess 1102c by a method such as brazing or diffusion bonding. A reinforcing plate 1120 of metal formed in an annular shape is loosely fit in the recess 1102c on the diaphragm 1114. The piezoelectric element 1112 is housed in the through-hole 1102h closed by the diaphragm 1114. On the rear side of the piezoelectric element 1112, the through-hole 1102h is closed by a bottom plate 1101 of metal formed in a disk shape. A disk-shaped shim 1116 of metal is provided between the piezoelectric element 1112 and the diaphragm 1114.

In the second case 1104, a circular shallow recess 1104c is formed on a face on a side mating with the first case 1102. The inner diameter of the recess 1104c is set to substantially the same size as the inner diameter of the reinforcing plate 1120 fit in the first case 1102. When the first case 1102 is assembled to the second case 1104, a substantially disk-shaped liquid chamber 1110 is formed by the diaphragm 1114 and the inner circumferential surface of the reinforcing plate 1120 provided on the first case 1102 side and the recess 1104c provided in the second case 1104. In the second case 1104, a supply passage 1104i for supplying the liquid from a side of the second case 1104 to the liquid chamber 1110 is provided. An ejection passage 1104o, through which the liquid pressurized in the liquid chamber 1110 passes, pierces the center position of the recess 1104c. In an opening portion of the ejection passage 1104o, the liquid ejection pipe 1106 is inserted and attached in the inner diameter portion thereof. The nozzle 1108 is formed at the distal end of the liquid ejection pipe 1106.

In the applicator 1100 in the first embodiment, the acceleration sensor 1130 that detects the acceleration of the applicator 1100 is provided. An output of the acceleration sensor 1130 is input to the control unit 1200 via a not-shown cable. In an example shown in FIGS. 2A and 2B, the acceleration sensor 1130 is provided in the second case 1104. However, the acceleration sensor 1130 may be provided in the first case 1102.

Figure 3:
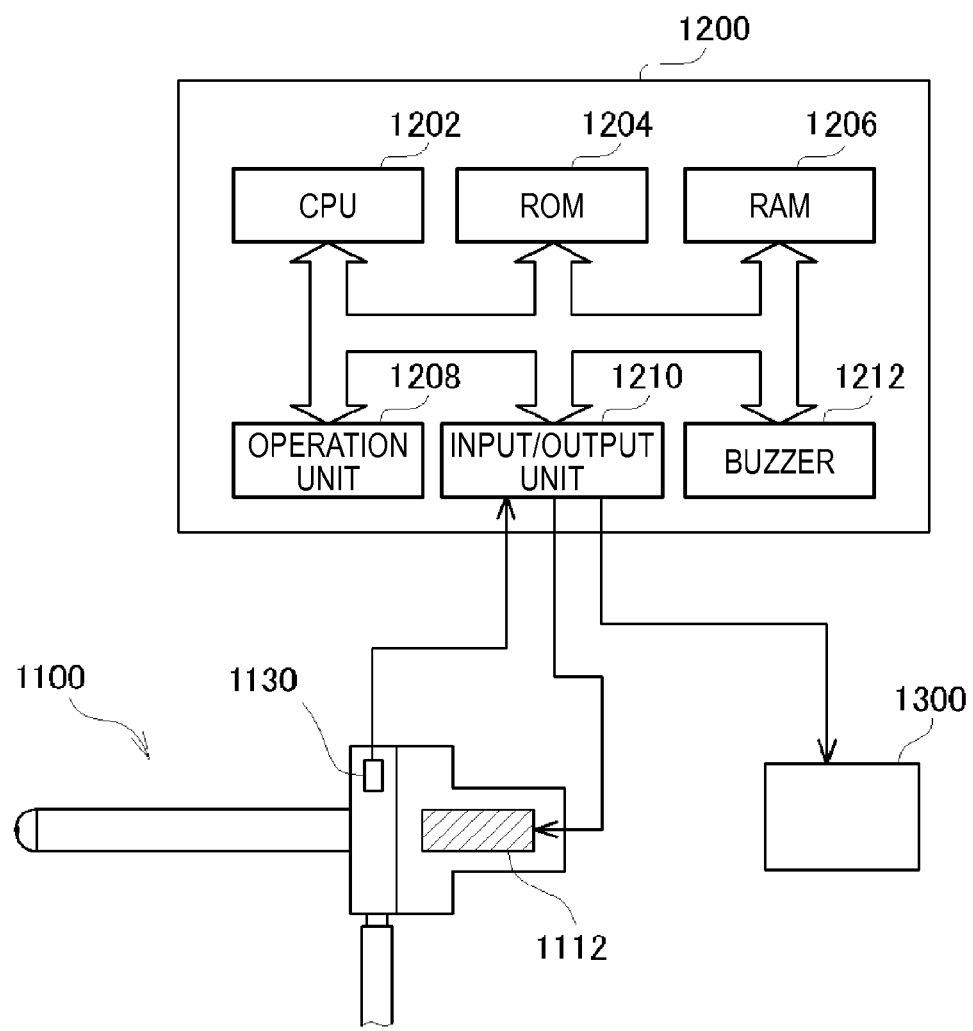
FIG. 3 is an explanatory diagram showing a rough configuration of a control unit in the first embodiment.

FIG. 3 is an explanatory diagram showing a rough configuration of the control unit 1200. The control unit 1200 is a microcomputer in which a CPU 1202, a ROM 1204, a RAM 1206, and the like are connected via a bus to be capable of exchanging data. In the control unit 1200, an operation unit 1208 operated by an operator of the medical apparatus 1010, an input/output unit 1210, a buzzer 1212, and the like are also provided. An output of the acceleration sensor 1130 is read from the input/output unit 1210 and stored in the RAM 1206. A driving voltage applied to the piezoelectric element 1112 and a control signal for controlling the operation of the liquid supply unit 1300 are output from the input/output unit 1210.

A-2. Operation Control Processing for the Medical Apparatus

Figure 4:
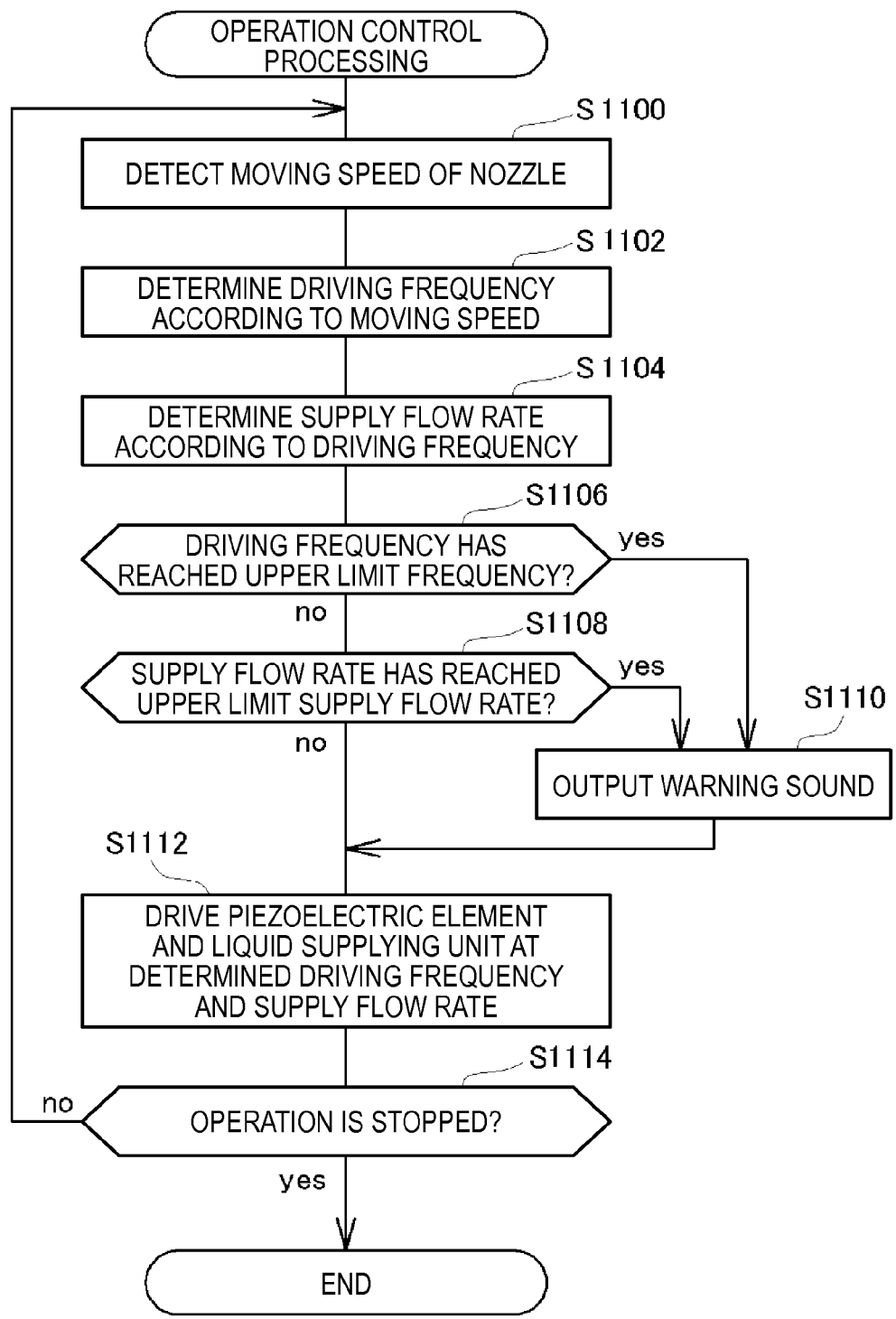
FIG. 4 is a flowchart of operation control processing executed by the control unit in the first embodiment.

FIG. 4 is a flowchart of operation control processing executed by the control unit 1200 to control the operation of the medical apparatus 1010 in the first embodiment. When a not-shown operation switch provided in the operation unit 1208 is operated by the operator of the medical apparatus 1010, the processing is executed after a predetermined initializing operation.

After starting the operation control processing, first, the control unit 1200 detects the moving speed of the nozzle 1108 on the basis of an output of the acceleration sensor 1130 mounted on the applicator 1100 (step S1100). That is, the moving speed of the nozzle 1108 includes a component generated by the swinging motion of the applicator 1100 and a component generated by the translating motion of the entire applicator 1100. The acceleration sensor 1130 that detects accelerations in translating directions and rotating directions of three axes orthogonal to one another (six directions in total) is mounted on the applicator 1100. If the accelerations are integrated, speeds of movement in three axis directions of the applicator 1100 and rotating speeds of the three axes are obtained. Therefore, the moving speed of the nozzle 1108 is detected on the basis of the speeds and the rotating speeds.

Subsequently, the control unit 1200 determines a driving frequency of the piezoelectric element 1112 (the number of times the driving voltage is applied to the piezoelectric element 1112 per unit time) according to the detected moving speed of the nozzle 1108 (step S1102). The control unit 1200 determines the driving frequency corresponding to the moving speed of the nozzle 1108 referring to a table stored in the ROM 1204 in advance.

Figures 5A, 5B:
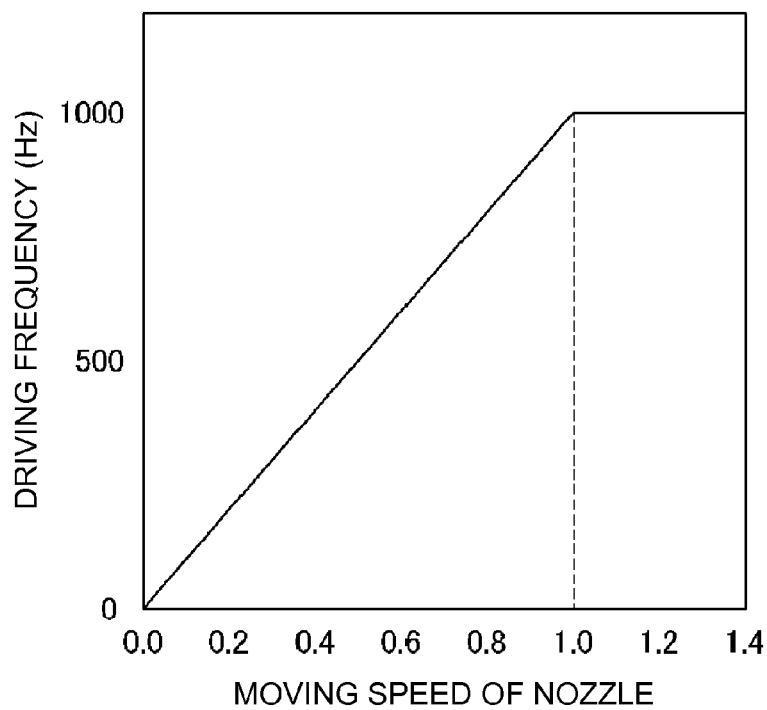
FIGS. 5A and 5B are explanatory diagrams conceptually showing a table in which driving frequencies corresponding to moving speeds of a nozzle are stored in the first embodiment.

FIGS. 5A and 5B are explanatory diagrams conceptually showing a table in which driving frequencies corresponding to moving speeds of the nozzles 1108 are stored. In FIG. 5A, data set in the table is shown. In FIG. 5B, contents of the table are represented by a graph. As shown in the figures, in a range until the moving speed of the nozzle 1108 reaches upper limit speed, the driving frequency is set to a value proportional to the moving speed of the nozzle 1108. Therefore, the number of pulses (the number of times of ejection of the liquid) per unit length of the nozzle 1108 is fixed irrespective of the moving speed of the nozzle 1108. After the moving speed of the nozzle 1108 reaches the upper limit speed, the driving frequency is retained at an upper limit frequency. In FIGS. 5A and 5B, the moving speed and the driving frequency are explained as being completely proportional to each other until the moving speed of the nozzle 1108 reaches the upper limit speed. However, the moving speed and the driving frequency only have to be roughly proportional to each other. It is also possible to slightly increase or decrease the driving frequency from a value proportional to the moving speed such that a more desirable result is obtained. In step S1102 of the operation control processing shown in FIG. 4, the control unit 1200 calculates a driving frequency corresponding to the moving speed of the nozzle 1108 obtained in step S1100 by interpolating the data set in the table. The moving speed of the nozzle and the driving frequency only have to keep a one-to-one relation. The moving speed and the driving frequency may have a relation other than direct proportion such as a relation by an Nth-degree function such as a quadratic function, a logarithmic relation, or a relation represented by a polygonal line. The same applies in the other embodiments and modifications thereof. In such a case, it is likely that the number of pulses per unit length is not always constant.

Subsequently, the control unit 1200 determines, according to the driving frequency, a supply flow rate of the liquid supplied from the liquid supply unit 1300 to the applicator 1100 (step S1104). The control unit 1200 determines the supply flow rate corresponding to the driving frequency referring to the table stored in the ROM 1204 in advance.

Figures 6A, 6B:
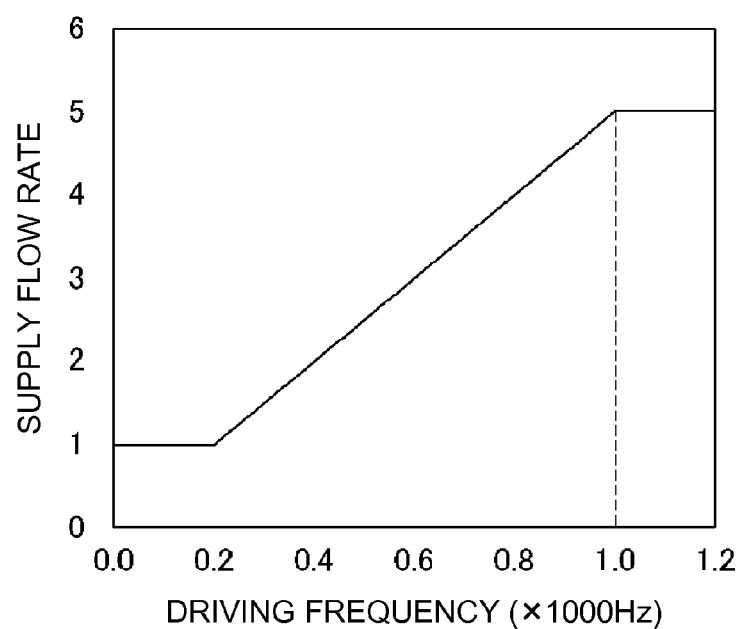
FIGS. 6A and 6B are explanatory diagrams conceptually showing a table in which supply flow rates corresponding to driving frequencies are stored in the first embodiment.

FIGS. 6A and 6B are explanatory diagrams conceptually showing a table in which supply flow rates corresponding to driving frequencies are stored. In FIG. 6A, data set in the table is shown. In FIG. 6B, contents of the table are represented by a graph. As shown in the figure, the supply flow rate is set to a value substantially proportional to the driving frequency. However, the supply flow rate is retained at a lower limit supply flow rate when the driving frequency is lower than a predetermined frequency (200 Hz). The supply flow rate is retained at an upper limit supply flow rate when the driving frequency is higher than a predetermined frequency (1000 Hz). In step S1104 of the operation control processing shown in FIG. 4, the supply flow rate corresponding to the driving frequency obtained in step S1102 is calculated by interpolating the data set in the table.

Thereafter, the control unit 1200 determines whether the driving frequency has reached the upper limit frequency (step S1106). When the driving frequency has reached the upper limit frequency (yes in step S1106), the control unit 1200 outputs warning sound from the buzzer 1212 (step S1110). On the other hand, when the driving frequency has not reached the upper limit frequency (no in step S1106), the control unit 1200 determines whether the supply flow rate has reached the upper limit supply flow rate (step S1108). When the supply flow rate has reached the upper limit supply flow rate (yes in step S1108), the control unit 1200 outputs the warning sound from the buzzer 1212 (step S1110). The warning sound output by the buzzer 1212 when the driving frequency reaches the upper limit frequency (yes in step S1106) and the warning sound output by the buzzer 1212 when the supply flow rate reaches the upper limit supply flow rate (yes in step S1108) may be different. Although the warning sound is output from the buzzer 1212, instead, a warning lamp may be lit, a warning screen may be displayed, or the applicator 1100 may be vibrated. The buzzer 1212 in the first embodiment corresponds to the "first informing unit" and the "second informing unit" in the invention. If correspondence between the driving frequency and the supply flow rate can be uniquely set according to a table, control processing for determining whether the driving frequency has reached the upper limit frequency or whether the supply flow rate has reached the upper limit supply flow rate may be adopted.

On the other hand, when the driving frequency does not reach the upper limit frequency (no in step S1106) and the supply flow rate does not reach the upper limit supply flow rate (no in step S1108), the control unit 1200 outputs control vibration to the liquid supply unit 1300 to apply the driving voltage to the piezoelectric element 1112 at the determined driving frequency and supply the liquid to the applicator 1100 at the determined supply flow rate (step S1112). Thereafter, the control unit 1200 determines whether the operation of the medical apparatus 1010 is stopped, i.e., whether the operator operates the operation unit 1208 of the control unit 1200 and operation stop of the medical apparatus 1010 is instructed (step S1114). As a result, when determining that the operation is not stopped (no in step S1114), the control unit 1200 returns to step S1100 and repeats the series of processing. On the other hand, when determining that the operation is stopped (yes in step S1114), the control unit 1200 ends the operation control processing shown in FIG. 4. In the medical apparatus 1010 in the first embodiment, the driving frequency is changed according to the moving speed of the nozzle 1108 as explained above. Therefore, it is possible to excise a biological tissue at stable excision depth. Explanation concerning this point is supplemented.

Figure 7A:
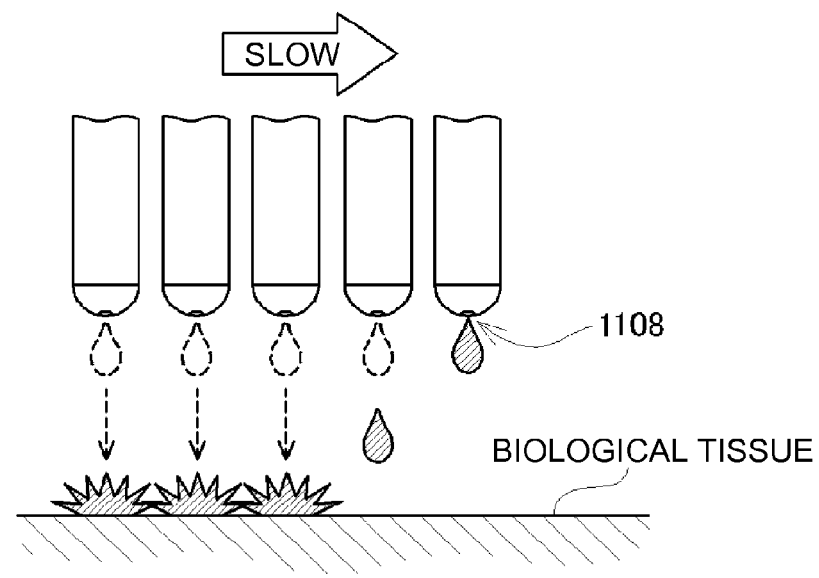
FIGS. 7A and 7B are explanatory diagrams of driving at the same driving frequency irrespective of the moving speed of the nozzle in the first embodiment.
Figure 7B:
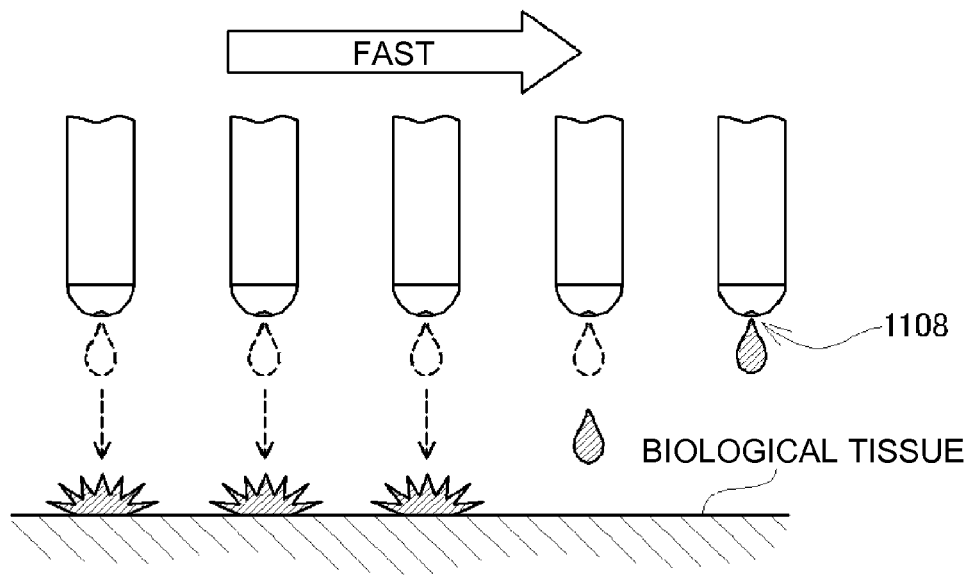

FIGS. 7A and 7B are explanatory diagrams of driving of the piezoelectric element 1112 at the same driving frequency irrespective of the moving speed of the nozzle 1108. In FIG. 7A, the moving speed of the nozzle 1108 is low. In FIG. 7B, the moving speed is high. If the driving frequency is the same, the number of times the liquid is ejected from the nozzle 1108 in a pulse-like manner per unit time is the same. Therefore, for example, as shown in FIG. 7B, when the moving speed of the nozzle 1108 increases, the liquid is sparsely ejected (the number of times the liquid is ejected per unit length decreases). As a result, the excision depth of the biological tissue is small in FIG. 7B compared with FIG. 7A. On the other hand, in this embodiment, since the driving frequency is increased when the moving speed of the nozzle 1108 increases, it is possible to keep the excision depth at the same depth. The same applies when the moving speed of the nozzle 1108 decreases. That is, when the moving speed of the nozzle 1108 decreases, since the liquid is densely ejected (the number of times the liquid is ejected per unit length increases), the excision depth of the biological tissue increases. On the other hand, in this embodiment, since the driving frequency is reduced when the moving speed of the nozzle 1108 decreases, it is possible to keep the excision depth.

The liquid ejected from the nozzle 1108 by the applicator 1100 is supplied from the liquid supply unit 1300. Therefore, in order to enable the liquid to be ejected from the nozzle 1108, the liquid needs to be supplied from the liquid supply unit 1300 at a necessary flow rate. However, there is an upper limit value (an upper limit supply flow rate) for the supply flow rate of the liquid supply unit 1300. In the medical apparatus 1010 in the first embodiment, the upper limit frequency is provided for the driving frequency. The warning sound is output when the driving frequency reaches the upper limit frequency or when the supply flow rate reaches the upper limit supply flow rate (step S1110 in FIG. 4). Therefore, the operator of the medical apparatus 1010 can easily recognize to that effect and operate the medical apparatus 1010 to prevent the moving speed of the applicator 1100 from exceeding the upper limit speed. Therefore, it is possible to prevent a situation in which the moving speed of the nozzle 1108 is excessively increased and an ejection amount per unit time of the liquid ejected from the nozzle 1108 exceeds the upper limit supply flow rate of the liquid supply unit 1300. If the liquid is about to be ejected at an ejection amount exceeding the upper limit supply amount of the liquid supply unit 1300, it is likely that the liquid cannot be ejected from the nozzle 1108 in a normal state and stable excision depth cannot be kept. However, according to this embodiment, it is possible to appropriately prevent such a problem.

B. Modifications in the First Embodiment

Several modifications are conceivable concerning the medical apparatus 1010 in the first embodiment. The modifications are briefly explained below.

B-1. First Modification in the First Embodiment

Figure 8:
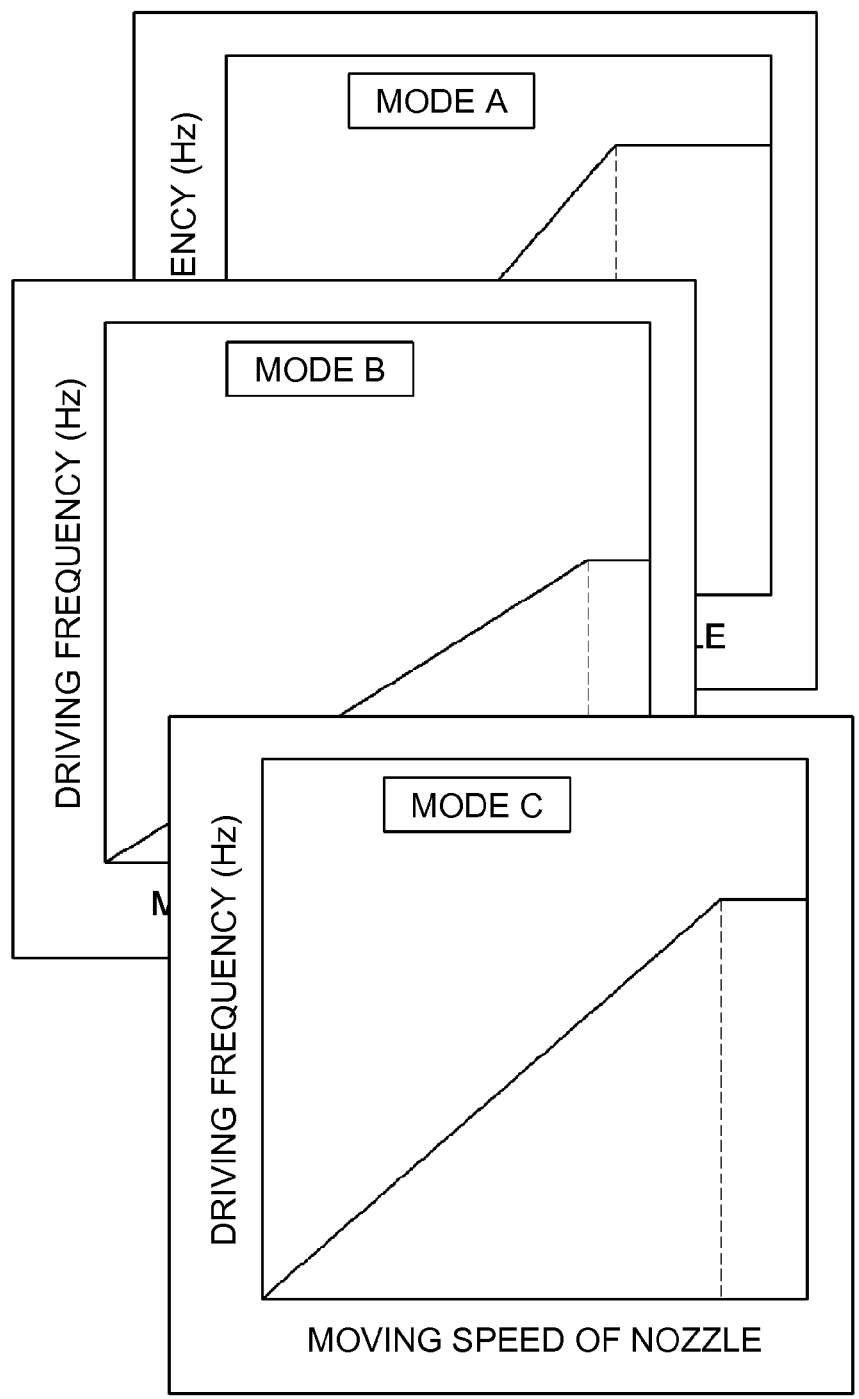
FIG. 8 is an explanatory diagram of a first modification in which a plurality of kinds of tables can be selected in the first embodiment.

In the explanation in the first embodiment, the driving frequency is uniquely determined according to the moving speed of the nozzle 1108. However, the operator of the medical apparatus 1010 may be able to select a driving frequency corresponding to the moving speed of the nozzle 1108 as appropriate by operating the operation unit 1208 of the control unit 1200. For example, as illustrated in FIG. 8, a plurality of kinds of tables in which driving frequencies corresponding to moving speeds of the nozzle 1108 are set are stored in the ROM 1204 of the control unit 1200 in advance. The operator of the medical apparatus 1010 may be able to designate a table by operating the operation unit 1208. Consequently, it is possible to excise the biological tissue at excision depth corresponding to the selected table irrespective of the moving speed of the nozzle 1108. The table in which driving frequencies corresponding to moving speeds of the nozzle 1108 are set corresponds to the "correspondence relation" in the invention. The ROM 1204 having stored there in the plurality of kinds of tables corresponds to the "correspondence-relation storing unit" in the invention. The operation unit 1208 operated by the operator to select a table stored in the ROM 1204 corresponds to the "correspondence-relation selecting unit" in the invention.

B-2. Second Modification in the First Embodiment

Figure 9:
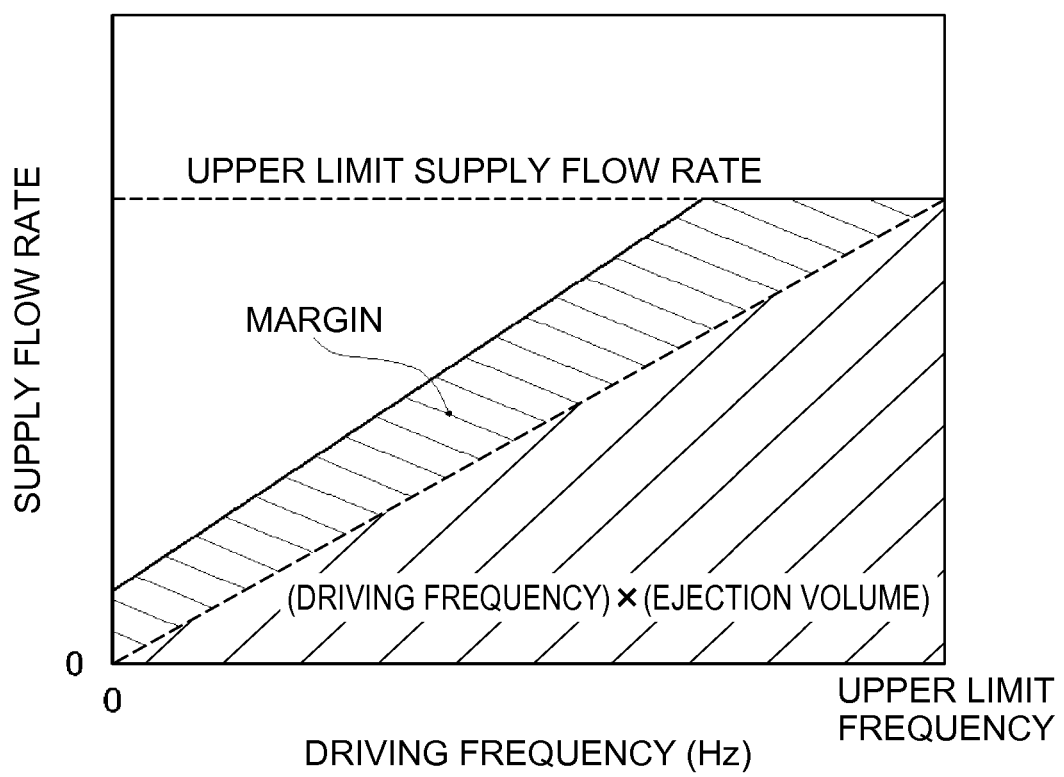
FIG. 9 is an explanatory diagram of a second modification in which a margin is set for a supply flow rate in the first embodiment.

In the explanation in the first embodiment, the supply flow rate of the liquid supplied to the applicator 1100 by the liquid supply unit 1300 is substantially proportional to the driving frequency. However, the supply flow rate may be set to always supply the liquid somewhat larger in quantity than the supply flow rate proportional to the driving frequency to the applicator 1100. In FIG. 9, a method of setting the supply flow rate is shown. In an example shown in the figure, the supply flow rate of the liquid supply unit 1300 with respect to the driving frequency is set as explained below. First, a margin (a margin flow rate) set in advance is added to a flow rate obtained by multiplying an ejection volume of the applicator 1100 (a volume of the liquid ejected by driving the piezoelectric element 1112 once) with the driving frequency. The supply flow rate may be set to be retained at the upper limit supply flow rate when an added-up value reaches the upper limit supply flow rate of the liquid supply unit 1300.

Consequently, even when the moving speed of the nozzle 1108 suddenly increases, it is possible to prevent a situation in which the liquid is in short supply. It is likely that, although the moving speed of the nozzle 1108 could suddenly change, a flow rate of the liquid supplied from the liquid supply unit 1300 to the applicator 1100 cannot suddenly change unlike the moving speed of the nozzle 1108. Even in such a situation, i.e., in time until a supply amount of the liquid from the liquid supply unit 1300 catches up with a supply amount considered necessary in calculation from the moving speed of the nozzle 1108, since the supply flow rate is set somewhat larger in advance, the liquid is not in short supply.

B-3. Third Modification in the First Embodiment

In the explanation in the first embodiment, the liquid is ejected from the nozzle 1108 in a pulse-like manner by applying the driving voltage to the piezoelectric element 1112 to reduce the capacity of the liquid chamber 1110. However, the liquid may be ejected from the nozzle 1108 in a pulse-like manner by irradiating laser light in a pulse like manner.

Figure 10:
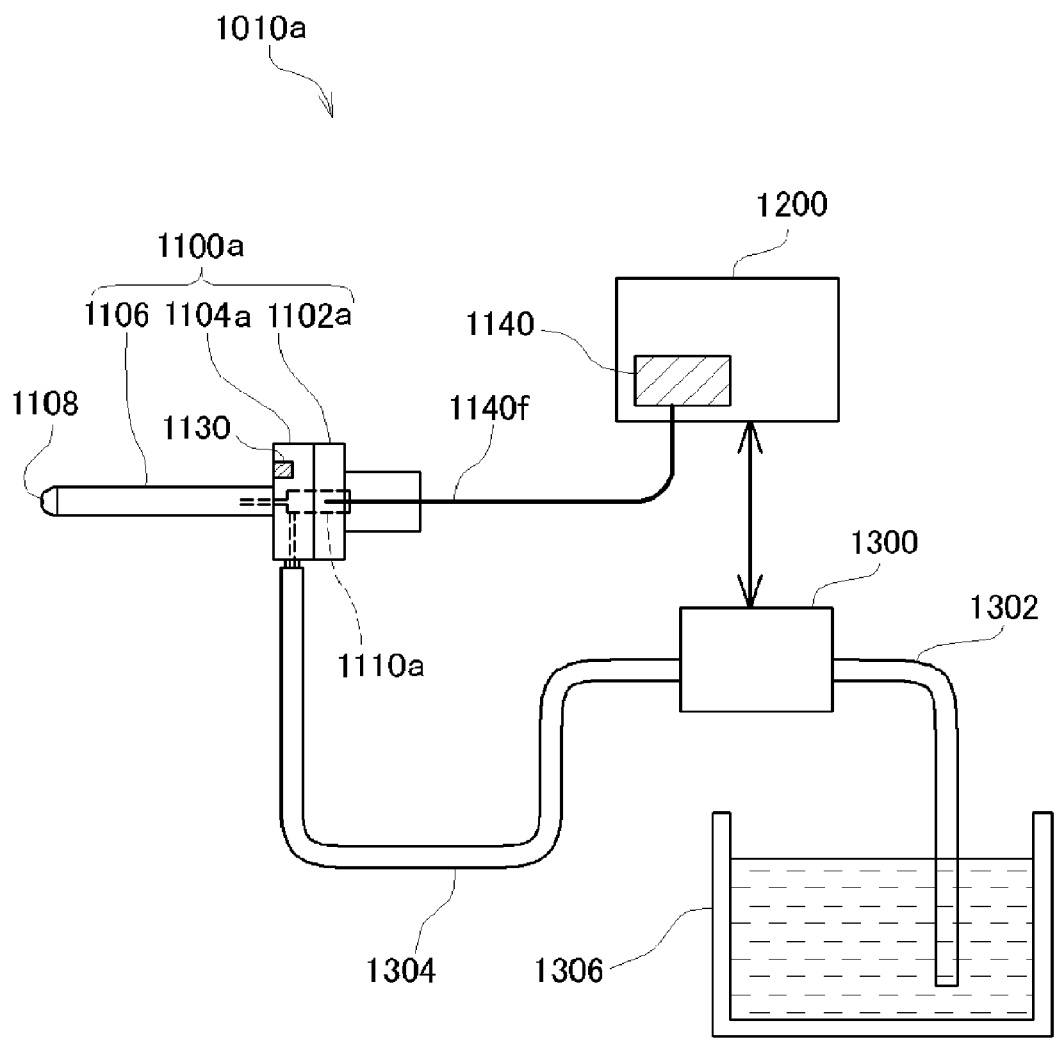
FIG. 10 is an explanatory diagram of a third modification in which liquid is ejected using a laser in the first embodiment.

In an example shown in FIG. 10, a laser oscillator 1140 is mounted in the control unit 1200. Laser light from the laser oscillator 1140 is guided to the liquid chamber 1110 through an optical fiber cable 1140f. In FIG. 10 and other modifications, members to be modified same as those in the embodiment (the first embodiment shown in FIG. 1) are denoted by the same reference numerals and signs and explanation of the members is omitted. In an applicator 1100a in this modification, the shape of a liquid chamber 1110a on the inside of a first case 1102a and a second case 1104a is different from the shape in the first embodiment. A terminal end of the optical fiber cable 1140f is arranged on the inside of the liquid chamber 1110a. In a medical apparatus 1010a in the third modification, a pulse-like laser is emitted from the laser oscillator 1140. The liquid in the liquid chamber 1110a is instantaneously boiled by laser light irradiated from the terminal end of the optical fiber cable 1140f. As a result, the liquid in the liquid chamber 1110a is pressurized. It is possible to eject the liquid from the nozzle 1108 in a pulse-like manner.

B-4. Fourth Modification in the First Embodiment

Figure 11:
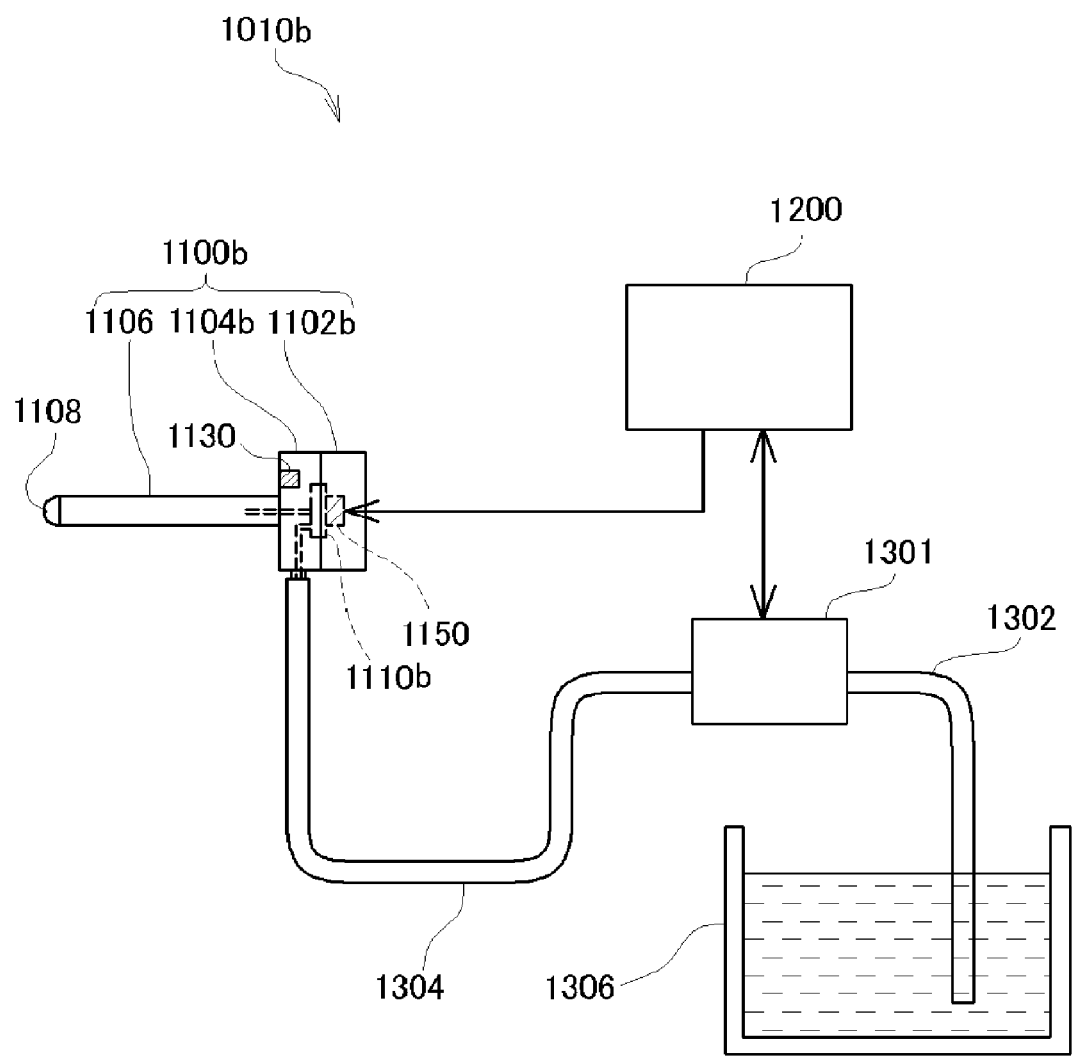
FIG. 11 is an explanatory diagram of a fourth modification in which liquid is ejected using a heater in the first embodiment.

A fourth modification of the first embodiment is shown in FIG. 11. In a medical apparatus 1010b in the fourth modification, as shown in the figure, a heater 1150 is provided in a liquid chamber 1110b of an applicator 1100b of the medical apparatus 1010b. A first case 1102b and a second case 1104b of the applicator 1100b are shaped to be capable of incorporating the heater 1150. The heater 1150 has an ability of generating heat when energized and reaching temperature for boiling the liquid in contact with the heater 1150 in a short time (substantially instantaneously).

In an example shown in FIG. 11, the heater 1150 is incorporated in the liquid chamber 1110b. An electric current can be supplied in a pulse-like manner from the control unit 1200 to the heater 1150. If the pulse-like electric current is fed to the heater 1150, the liquid in a portion in contact with the heater 1150 in the liquid chamber 1110b can be instantaneously boiled. Therefore, it is possible to pressurize the liquid in the liquid chamber 1110b. As a result, it is possible to eject the liquid in a pulse-like manner from the nozzle 1108.

C. Second Embodiment

C-1. Apparatus Configuration

Figure 12:
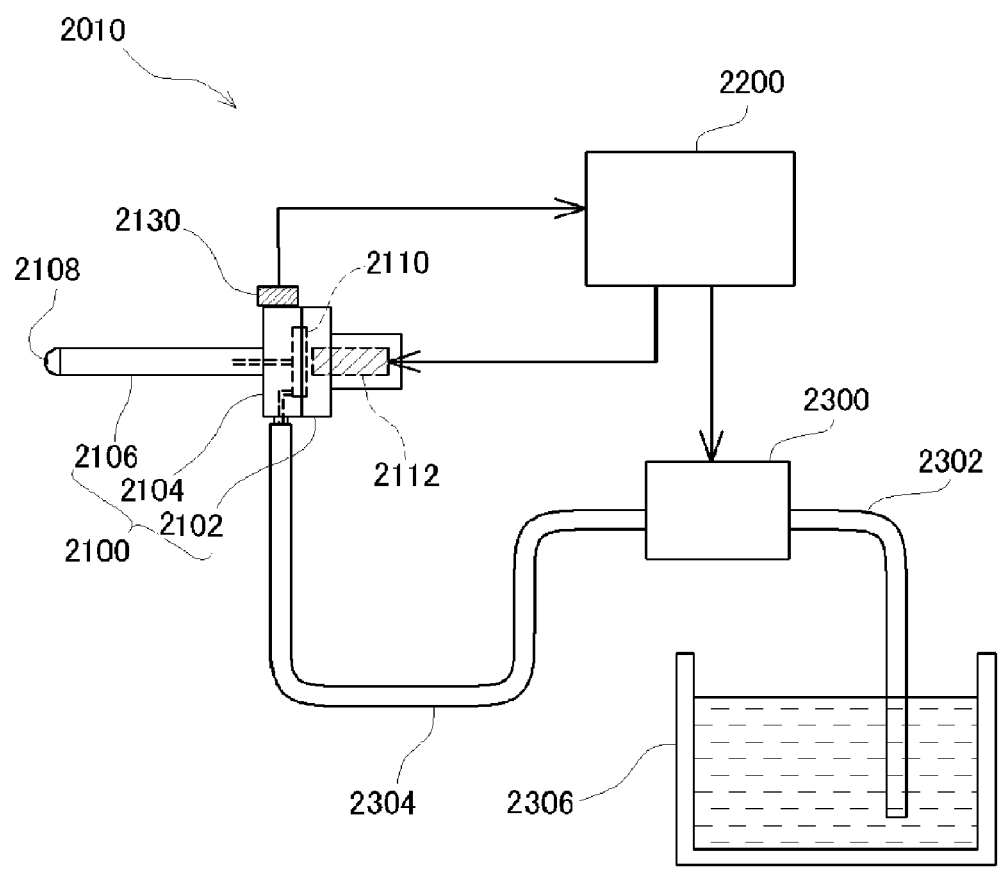
FIG. 12 is an explanatory diagram showing a rough configuration of a medical apparatus according to a second embodiment.

A second embodiment of the invention is explained. FIG. 12 is an explanatory diagram showing a rough configuration of a medical apparatus 2010 according to the second embodiment. The medical apparatus 2010 shown in the figure is used for a surgical operation method for incising or excising a biological tissue by ejecting liquid such as water or saline to the biological tissue.

As shown in the figure, the medical apparatus 2010 in the second embodiment includes an applicator 2100 held by an operator by hand and operated to eject liquid, a liquid supply unit 2300 configured to supply the liquid to the applicator 2100, a liquid container 2306 configured to store the liquid to be ejected, and a control unit 2200 configured to control the operation of the applicator 2100 and the liquid supply unit 2300.

The applicator 2100 includes a first case 2102, a second case 2104 attached to the first case 2102, a liquid ejection pipe 2106 provided to project from the second case 2104 to the opposite side of the first case 2102, and a nozzle 2108 provided at the distal end of the liquid ejection pipe 2106. A liquid chamber 2110 is formed on a mating face of the first case 2102 and the second case 2104. A liquid supply unit 2300 is connected to the liquid chamber 2110 via a second connection tube 2304. The liquid supply unit 2300 is connected to the liquid container 2306 via a first connection tube 2302. When the liquid supply unit 2300 is actuated, the liquid in the liquid container 2306 is supplied to the liquid chamber 2110. The first case 2102 and the second case 2104 in the second embodiment correspond to the "liquid ejecting unit" in the invention.

A laminated piezoelectric element 2112 is housed in the first case 2102. As explained in detail below, when a voltage is applied to the piezoelectric element 2112 from the control unit 2200, the liquid in the liquid chamber 2110 is ejected from the nozzle 2108 in a pulse-like manner. The piezoelectric element 2112 in the second embodiment corresponds to the "pulsation generating unit" in the invention.

A camera 2130 is provided in the applicator 2100. The camera 2130 photographs an image of the vicinity of the tip of the nozzle 2108 at every predetermined time interval. The image photographed by the camera 2130 is input to the control unit 2200. As explained in detail below, the control unit 2200 detects the moving speed of the nozzle 2108 on the basis of an analysis result of the photographed image. The control unit 2200 controls, according to the moving speed of the nozzle 2108, the number of times a driving voltage is applied to the piezoelectric element 2112 per unit time (a driving frequency). The camera 2130 in the second embodiment corresponds to the "photographing unit" in the invention. The control unit 2200 in the second embodiment corresponds to the "pulsation-generation control unit" in the invention.

FIGS. 13A and 13B are explanatory diagrams showing detailed structure of the applicator 2100. An exploded sectional view of the applicator 2100 is shown in FIG. 13A. A sectional view after assembly is shown in FIG. 13B. In the first case 2102, a large circular shallow recess 2102c is formed substantially in the center of a face mating with the second case 2104. A through-hole 2102h circular in section is formed in the center position of the recess 2102c to pierce through the first case 2102.

A thin diaphragm 2114 of metal is provided in the bottom of the recess 2102c to close the through-hole 2102h. The peripheral edge portion of the diaphragm 2114 is hermetically fixedly attached to the bottom of the recess 2102c by a method such as brazing or diffusion bonding. A reinforcing plate 2120 of metal formed in an annular shape is loosely fit in the recess 2102c on the diaphragm 2114. The piezoelectric element 2112 is housed in the through-hole 2102h closed by the diaphragm 2114. On the rear side of the piezoelectric element 2112, the through-hole 2102h is closed by a bottom plate 2101 of metal formed in a disk shape. A disk-shaped shim 2116 of metal is provided between the piezoelectric element 2112 and the diaphragm 2114.

In the second case 2104, a circular shallow recess 2104c is formed on a face on a side mating with the first case 2102. The inner diameter of the recess 2104c is set to substantially the same size as the inner diameter of the reinforcing plate 2120 fit in the first case 2102. When the first case 2102 is assembled to the second case 2104, a substantially disk-shaped liquid chamber 2110 is formed by the diaphragm 2114 and the inner circumferential surface of the reinforcing plate 2120 provided on the first case 2102 side and the recess 2104c provided in the second case 2104. In the second case 2104, a supply passage 2104i for supplying the liquid from a side of the second case 2104 to the liquid chamber 2110 is provided. An ejection passage 2104o, through which the liquid pressurized in the liquid chamber 2110 passes, pierces the center position of the recess 2104c. In an opening portion of the ejection passage 2104o, the liquid ejection pipe 2106 is inserted and attached in the inner diameter portion thereof. The nozzle 2108 is formed at the distal end of the liquid ejection pipe 2106.

In the applicator 2100 in the second embodiment, the camera 2130 configured to photograph an image of the vicinity of the tip of the nozzle 2108 is provided. An output (i.e., a photographed image) of the camera 2130 is input to the control unit 2200 via a not-shown cable. In an example shown in FIGS. 13A and 13B, the camera 2130 is provided in the second case 2104. However, the camera 2130 may be provided in the first case 2102.

In the applicator 2100 having such a configuration, when a voltage is applied to the piezoelectric element 2112 to expand the piezoelectric element 2112, the diaphragm 2114 is deformed and the capacity of the liquid chamber 2110 decreases. When the voltage applied to the piezoelectric element 2112 is released, the diaphragm 2114 is restored from the deformation and the capacity of the liquid chamber 2110 returns to the original capacity. Therefore, when the driving voltage is applied to the piezoelectric element 2112 and the capacity of the liquid chamber 2110 is reduced while the liquid is supplied to the liquid chamber 2110, the liquid in the liquid chamber 2110 is pressurized and ejected from the nozzle 2108 in a pulse-like manner. When the voltage applied to the piezoelectric element 2112 is released and the capacity of the liquid chamber 2110 is returned to the original capacity, the liquid equivalent to the ejected amount is supplied into the liquid chamber 2110. When the driving voltage is applied to the piezoelectric element 2112 again in this state, the capacity of the liquid chamber 2110 decreases and the liquid in the liquid chamber 2110 is ejected from the nozzle 2108 in a pulse-like manner. Therefore, the driving voltage is applied to the piezoelectric element 2112 at a predetermined driving frequency, whereby the liquid in the liquid chamber 2110 pulsates and the pulse-like liquid is ejected from the nozzle 2108 at a fixed period. The pulse-like ejection of the liquid means ejection of the liquid at a regularly or irregularly fluctuating flow rate or moving speed of the liquid to be ejected. Examples of the pulse-like ejection include intermittent ejection for repeating ejection and non-ejection of the liquid. However, the flow rate or the moving speed of the liquid to be ejected only has to regularly or irregularly fluctuate. The pulse-like ejection does not always need to be the intermittent ejection.

When a biological tissue is incised or excised while the pulse-like liquid is ejected at a fixed period, depth of excision of the biological tissue (excision depth) changes according to speed at which the operator moves the position of the nozzle 2108. A reason for the change is as explained below.

Figure 14A:
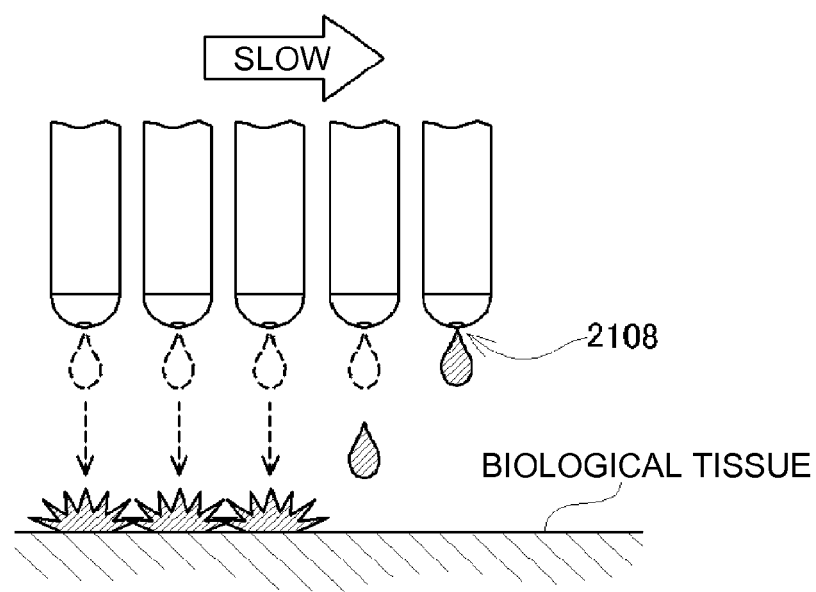
FIGS. 14A and 14B are explanatory diagrams showing a mechanism in which excision depth of a biological tissue changes according to the moving speed of a nozzle in the second embodiment.
Figure 14B:
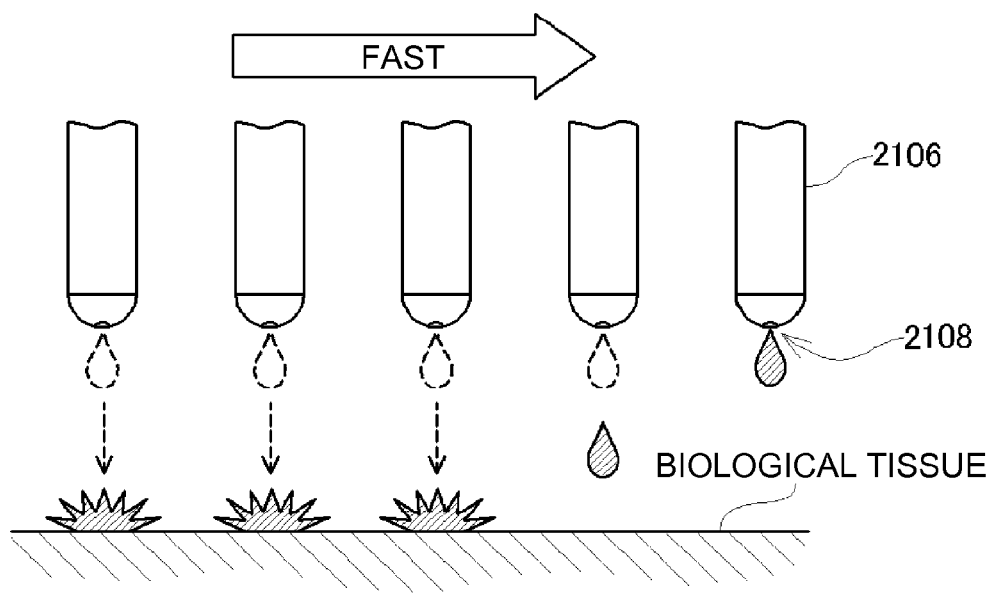

FIGS. 14A and 14B are explanatory diagrams showing a mechanism in which the excision depth of the biological tissue changes according to the moving speed of the nozzle 2108. In FIG. 14A, the moving speed of the nozzle 2108 is low. In FIG. 14B, the moving speed of the nozzle 2108 is high. If the driving frequency for applying the driving voltage to the piezoelectric element 2112 is the same, the number of times the liquid is ejected from the nozzle 2108 in a pulse-like manner per unit time is the same. Therefore, for example, as shown in FIG. 14B, when the moving speed of the nozzle 2108 increases, the liquid is sparsely ejected (the number of times the liquid is ejected per unit length decreases). As a result, the excision depth of the biological tissue is small in FIG. 14B compared with FIG. 14A. The same applies when the moving speed of the nozzle 2108 decreases. That is, when the moving speed of the nozzle 2108 decreases, since the liquid is densely ejected (the number of times the liquid is ejected per unit length increases), the excision depth of the biological tissue increases.

When the excision depth of the biological tissue changes according to the speed for moving the nozzle 2108 as explained above, it is difficult to excise the biological tissue at stable depth. When the operator does not remember that the operator changed the moving speed of the nozzle 2108, the operator undesirably misunderstands that the sharpness of the medical apparatus 2010 has changed. Therefore, in the medical apparatus 2010 in the second embodiment, the driving of the piezoelectric element 2112 is controlled as explained below, whereby the excision depth of the biological tissue is prevented from changing according to the moving speed of the nozzle 2108.

Figure 15:
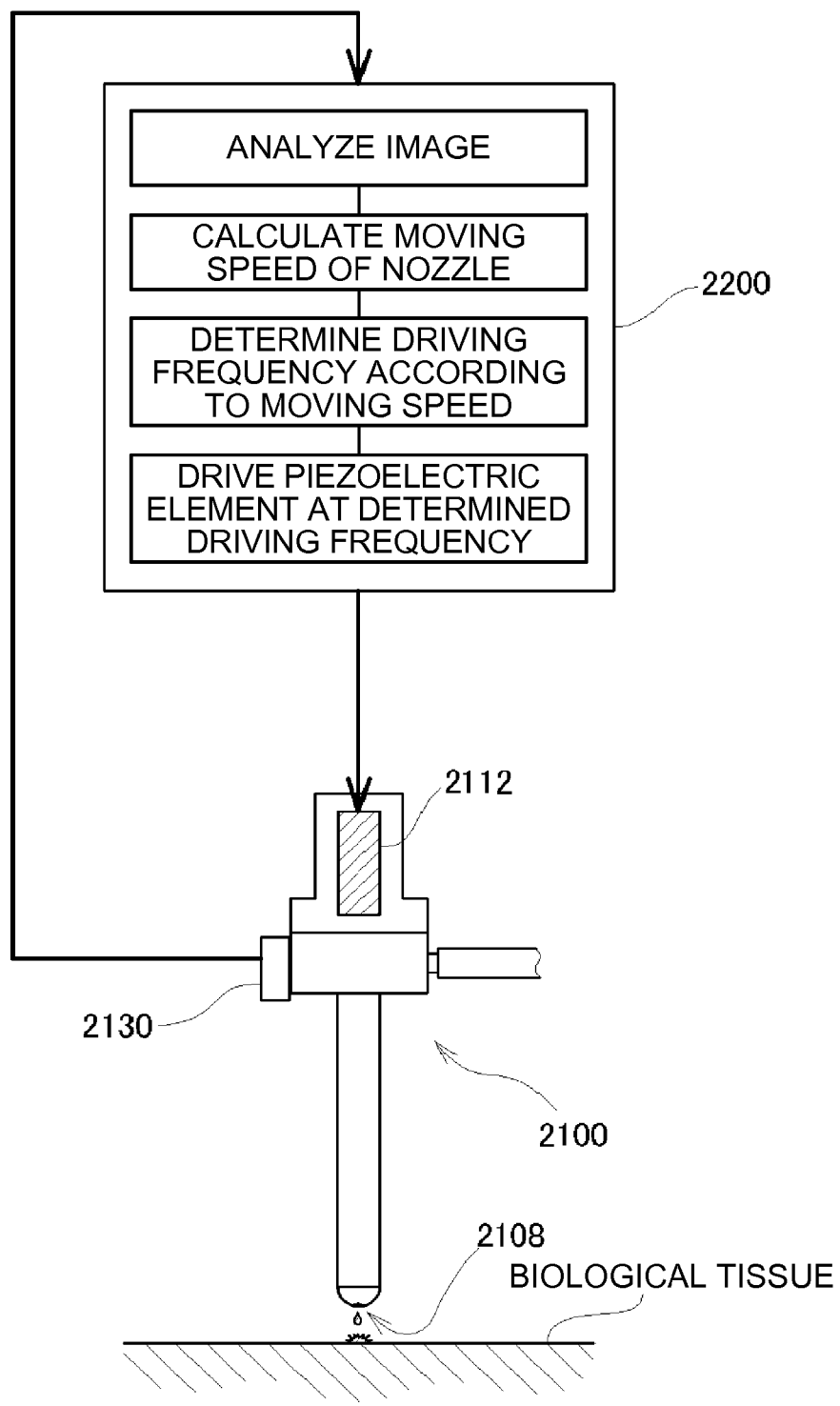
FIG. 15 is a block diagram showing a method in which a control unit controls driving of a piezoelectric element in the second embodiment.

FIG. 15 is a block diagram showing a method in which the control unit 2200 controls the driving of the piezoelectric element 2112 in the second embodiment. As shown in the figure, the camera 2130 is provided in the applicator 2100 in the second embodiment. While the applicator 2100 is operated to incise or excise the biological tissue, an image of the vicinity of the tip of the nozzle 2108 (an image of the vicinity of a collision place of the liquid) is photographed by the camera 2130 at a predetermined time interval. When the photographed image is input to the control unit 2200, the control unit 2200 analyzes the input image and calculates moving speed of the nozzle 2108 on the basis of an analysis result.

The control unit 2200 calculates moving speed of the nozzle 2108 as explained below. First, the control unit 2200 reads out an image photographed immediately before an image photographed this time. The camera 2130 photographs an image of the vicinity of the tip of the nozzle 2108 at the predetermined time interval. The photographed image is stored in a RAM (not shown in the figure) of the control unit 2200. Therefore, the control unit 2200 reads out an image photographed last time from the RAM of the control unit 2200.

After reading out the image photographed last time, the control unit 2200 detects, according to image correlation, out of the image photographed this time, an image pattern similar to a predetermined image pattern in the image photographed last time. A time interval of the photographing of an image by the camera 2130 is set sufficiently short. Therefore, an image pattern similar to the predetermined image pattern in the image photographed last time is surely detected out of the image photographed this time.

After detecting the image pattern similar to the predetermined image pattern out of the image photographed this time, the control unit 2200 detects a moving distance of the image pattern. On the image, it is seen by how many pixels the image pattern moves. Therefore, the control unit 2200 detects the moving distance of the image pattern by converting the number of pixels the image pattern moves into an actual distance. The moving distance of the image pattern detected in this way is equivalent to the moving distance of the nozzle 2108 (accurately, a moving distance of the collision place of the liquid). Therefore, the control unit 2200 calculates moving speed of the nozzle 2108 by dividing the moving distance by the photographing time interval of the camera 2130.

The control unit 2200 in the second embodiment compares images obtained at the predetermined time interval to thereby detect, on the image, a moving distance of the collision place of the liquid and calculates moving speed of the nozzle on the basis of the moving distance. Therefore, the control unit 2200 in the second embodiment corresponds to the "moving-distance detecting unit" and the "moving-speed detecting unit" in the invention.

After calculating the moving speed of the nozzle 2108, the control unit 2200 determines a driving frequency of the piezoelectric element 2112 according to the moving speed. The control unit 2200 determines the driving frequency corresponding to the moving speed of the nozzle 2108 referring to a table explained below stored in advance in a ROM (not shown in the figure) of the control unit 2200.

Figures 16, 17:
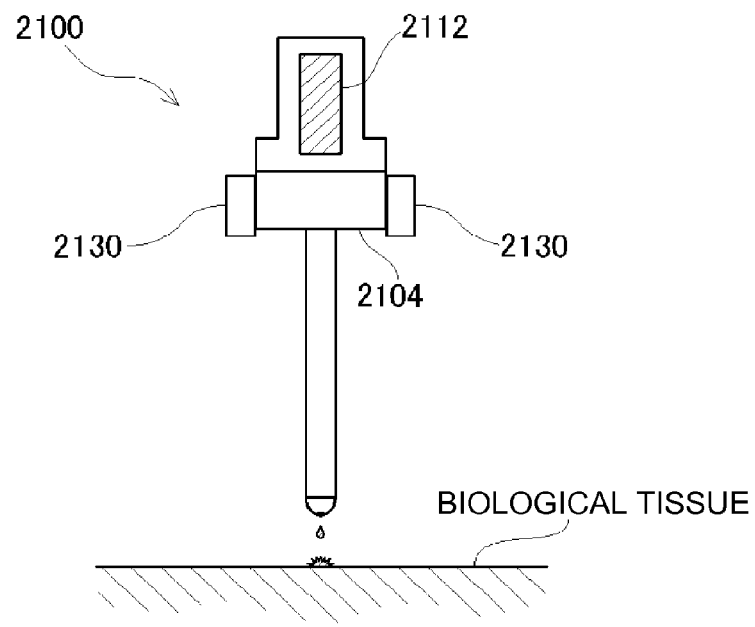
FIG. 16 is an explanatory diagram conceptually showing a table in which driving frequencies corresponding to moving speeds of the nozzle are stored in the second embodiment.
FIG. 17 is an explanatory diagram showing rough structure of an applicator in a first modification in the second embodiment.

FIG. 16 is an explanatory diagram conceptually showing a table in which driving frequencies corresponding to moving speeds of the nozzle 2108 are stored. As shown in the figure, in a range until the moving speed of the nozzle 2108 reaches upper limit speed, the driving frequency is set to a value proportional to the moving speed of the nozzle 2108. Therefore, the number of pulses (the number of times of ejection of the liquid) per unit length of the nozzle 2108 is fixed irrespective of the moving speed of the nozzle 2108. After the moving speed of the nozzle 2108 reaches the upper limit speed, the driving frequency is retained at an upper limit frequency. Therefore, a situation is avoided in which the value of the driving frequency is excessively large and the supply of the liquid to the liquid chamber 2110 does not catch up with a necessary supply amount and, as a result, the liquid cannot be ejected from the nozzle 2108. In FIG. 16, the moving speed and the driving frequency are explained as being completely proportional to each other until the moving speed of the nozzle 2108 reaches the upper limit speed. However, the moving speed and the driving frequency only have to be roughly proportional to each other. It is also possible to slightly increase or decrease the driving frequency from a value proportional to the moving speed such that a more desirable result is obtained.

After determining the driving frequency of the piezoelectric element 2112 referring to the table explained above, as shown in FIG. 15, the control unit 2200 drives the piezoelectric element 2112 at the determined driving frequency. In this way, the control unit 2200 in the second embodiment calculates, every time an image is input from the camera 2130, moving speed of the nozzle 2108 on the basis of the input image and drives the piezoelectric element 2112 at a driving frequency corresponding to the moving speed.

By performing such control, in the medical apparatus 2010 in the second embodiment, it is possible to increase the driving frequency of the piezoelectric element 2112 when the moving speed of the nozzle 2108 increases and reduce the driving frequency when the moving speed of the nozzle 2108 decreases. As a result, even if the moving speed of the nozzle 2108 changes, it is possible to fix the number of times of ejection of the liquid per unit length of the nozzle 2108. Therefore, it is possible to excise the biological tissue at stable excision depth.

D. Modifications of the Second Embodiment

Several modifications are conceivable concerning the medical apparatus 2010 in the second embodiment. The modifications are briefly explained below. In the modifications explained below, components same as those in the second embodiment are denoted by reference numerals and signs same as those in the second embodiment and detailed explanation of the components is omitted.

D-1. First Modification in the Second Embodiment

In the explanation in the second embodiment, the one camera 2130 is provided in the applicator 2100 and moving speed of the nozzle 2108 is calculated by analyzing an image photographed by the camera 2130. On the other hand, a plurality of cameras 2130 may be provided in the applicator 2100 and moving speed of the nozzle 2108 may be calculated by analyzing images photographed from a plurality of directions by the plurality of cameras 2130.

FIG. 17 is an explanatory diagram showing rough structure of the applicator 2100 in a first modification. In the applicator 2100 in the first modification, the cameras 2130 are provided in a plurality of places (two places in an example shown in FIG. 17) of the second case 2104. In the medical apparatus 2010 in the first modification including the applicator 2100, images of the vicinity of the tip of the nozzle 2108 are photographed using the two cameras 2130. It is possible to detect a distance from the tip of the nozzle 2108 to the collision place of the liquid by detecting a shift amount (a parallax amount) of two images photographed in this way.

If the distance from the tip of the nozzle 2108 to the collision place of the liquid is known, it is possible to convert a moving distance of the nozzle 2108 on the images into an actual moving distance taking into account the distance. Therefore, it is possible to accurately detect a moving distance of the nozzle 2108 and improve detection accuracy for moving speed of the nozzle 2108. As a result, it is possible to excise a biological tissue at more stable excision depth by driving the piezoelectric element 2112 at a driving frequency corresponding to the moving speed of the nozzle 2108.

D-2. Second Modification in the Second Embodiment

In the explanation in the second embodiment and the first modification, the camera 2130 is fixed to the applicator 2100. However, the camera 2130 may be provided detachably attachable to the applicator 2100.

Figure 18:
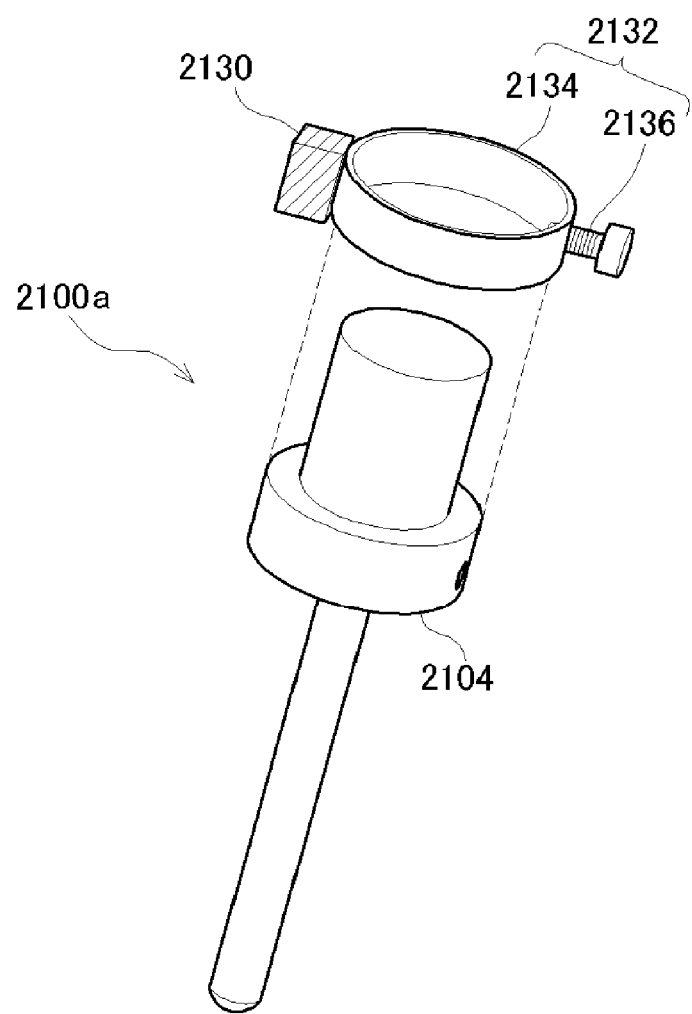
FIG. 18 is an explanatory diagram showing rough structure of an applicator in a second modification in the second embodiment.

FIG. 18 is an explanatory diagram showing rough structure of an applicator 2100a in a second modification. In the applicator 2100a in the second modification shown in the figure, the camera 2130 is attached to the applicator 2100a via an attachment section 2132. The attachment section 2132 includes an annular member 2134 having an inner diameter same as the outer diameter of the second case 2104 and a screw 2136 provided in the annular member 2134. The camera 2130 is fixed to the outer circumferential surface of the annular member 2134 by means such as bonding or screwing. When the annular member 2134 of the attachment section 2132 is fit in the second case 2104 and the screw 2136 is tightened, the camera 2130 is attached to the applicator 2100a.

The applicator 2100a is sometimes configured to be disposable taking sanitation into account. Even in such a case, if the camera 2130 is detachably attachable to the applicator 2100a, it is possible to detach the expensive camera 2130 from the applicator 2100a to be discarded and attach the camera 2130 to a new applicator 2100a (reuse the camera 2130). As a result, it is possible to reduce running cost of the medical apparatus.

D-3. Third Modification in the Second Embodiment

In the explanation in the second embodiment, the liquid is ejected from the nozzle 2108 in a pulse-like manner by applying the driving voltage to the piezoelectric element 2112 and reducing the capacity of the liquid chamber 2110. However, the liquid may be ejected from the nozzle 2108 in a pulse-like manner by irradiating laser light in a pulse-like manner.

Figure 19:
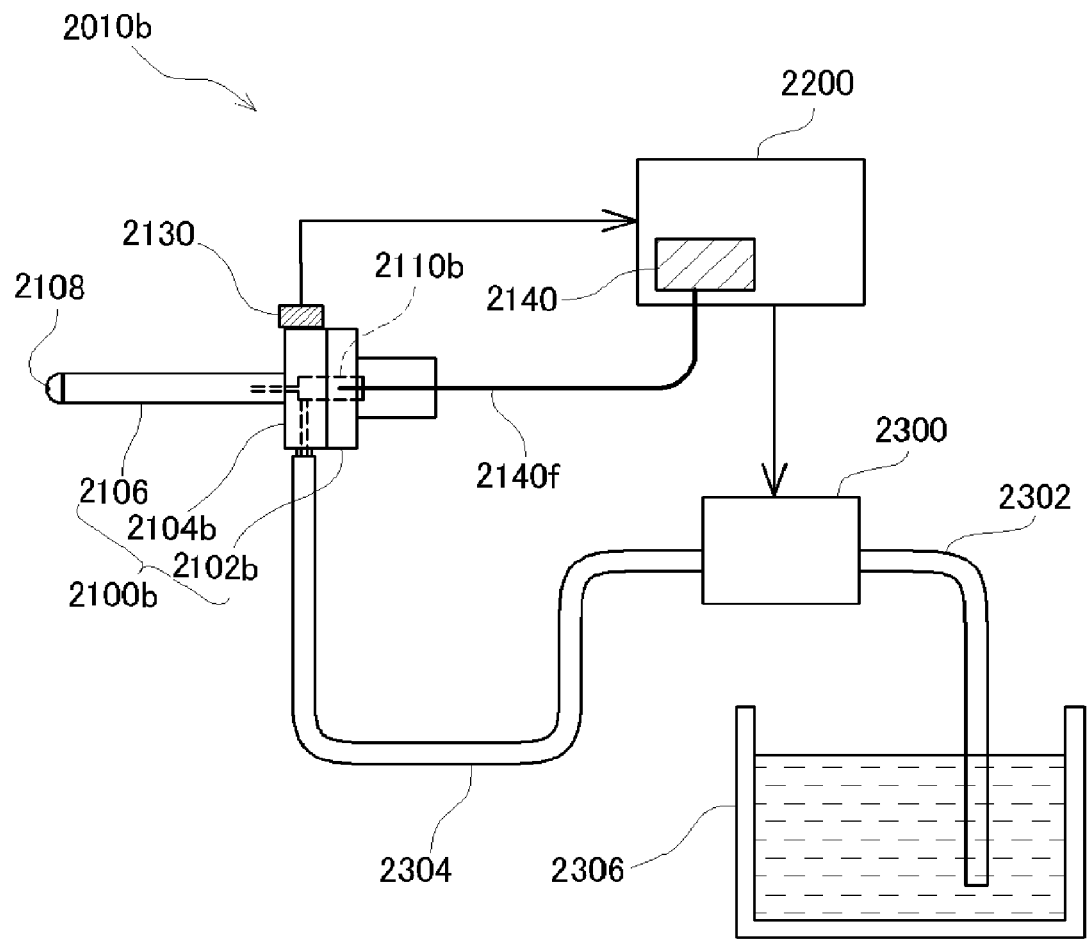
FIG. 19 is an explanatory diagram of a third modification in which liquid is ejected using a laser in the second embodiment.

In an example shown in FIG. 19, a laser oscillator 2140 is mounted in the control unit 2200. Laser light from the laser oscillator 2140 is guided to a liquid chamber 2110b through an optical fiber cable 2140f. In an applicator 2100b in this modification, the shape of the liquid chamber 2110b on the inside of a first case 2102a and a second case 2104b is different from the shape in the second embodiment. A terminal end of the optical fiber cable 2140f is arranged on the inside of the liquid chamber 2100b. In a medical apparatus 2010b in the third modification, a pulse-like laser is emitted from the laser oscillator 2140. The liquid on which the laser is irradiated in the liquid chamber 2110b is instantaneously boiled. As a result, the liquid in the liquid chamber 2110b is pressurized. It is possible to eject the liquid from the nozzle 2108 in a pulse-like manner.

D-4. Fourth Modification in the Second Embodiment

Figure 20:
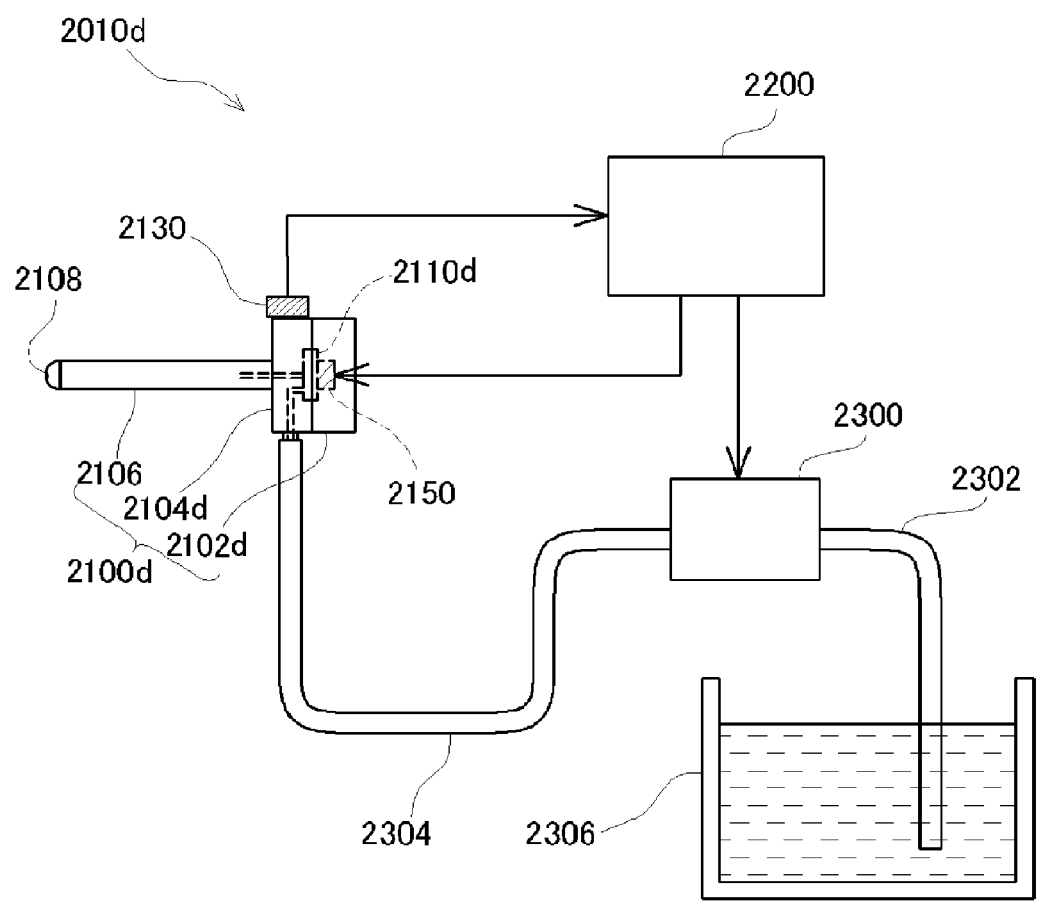
FIG. 20 is an explanatory diagram of a fourth modification in which liquid is ejected using a heater in the second embodiment.

A configuration in a fourth modification of the second embodiment is shown in FIG. 20. In a medical apparatus 2010d in the fourth modification, as shown in the figure, a heater 2150 is provided in a liquid chamber 2110d of an applicator 2100d of the medical apparatus 2010d. A first case 2102d and a second case 2104d of the applicator 2100d are shaped to be capable of incorporating the heater 2150. The heater 2150 has an ability of generating heat when energized and reaching temperature for boiling the liquid in contact with the heater 2150 in a short time (substantially instantaneously).

In an example shown in FIG. 20, the heater 2150 is incorporated in a part of the liquid chamber 2110d. An electric current can be supplied in a pulse-like manner from the control unit 2200 to the heater 2150. If the pulse-like electric current is fed to the heater 2150, the liquid in a portion in contact with the heater 2150 in the liquid chamber 2110d can be instantaneously boiled. Therefore, it is possible to pressurize the liquid in the liquid chamber 2110d. As a result, it is possible to eject the liquid in a pulse-like manner from the nozzle 2108.

E. Third Embodiment

E-1. Apparatus Configuration

Figure 21:
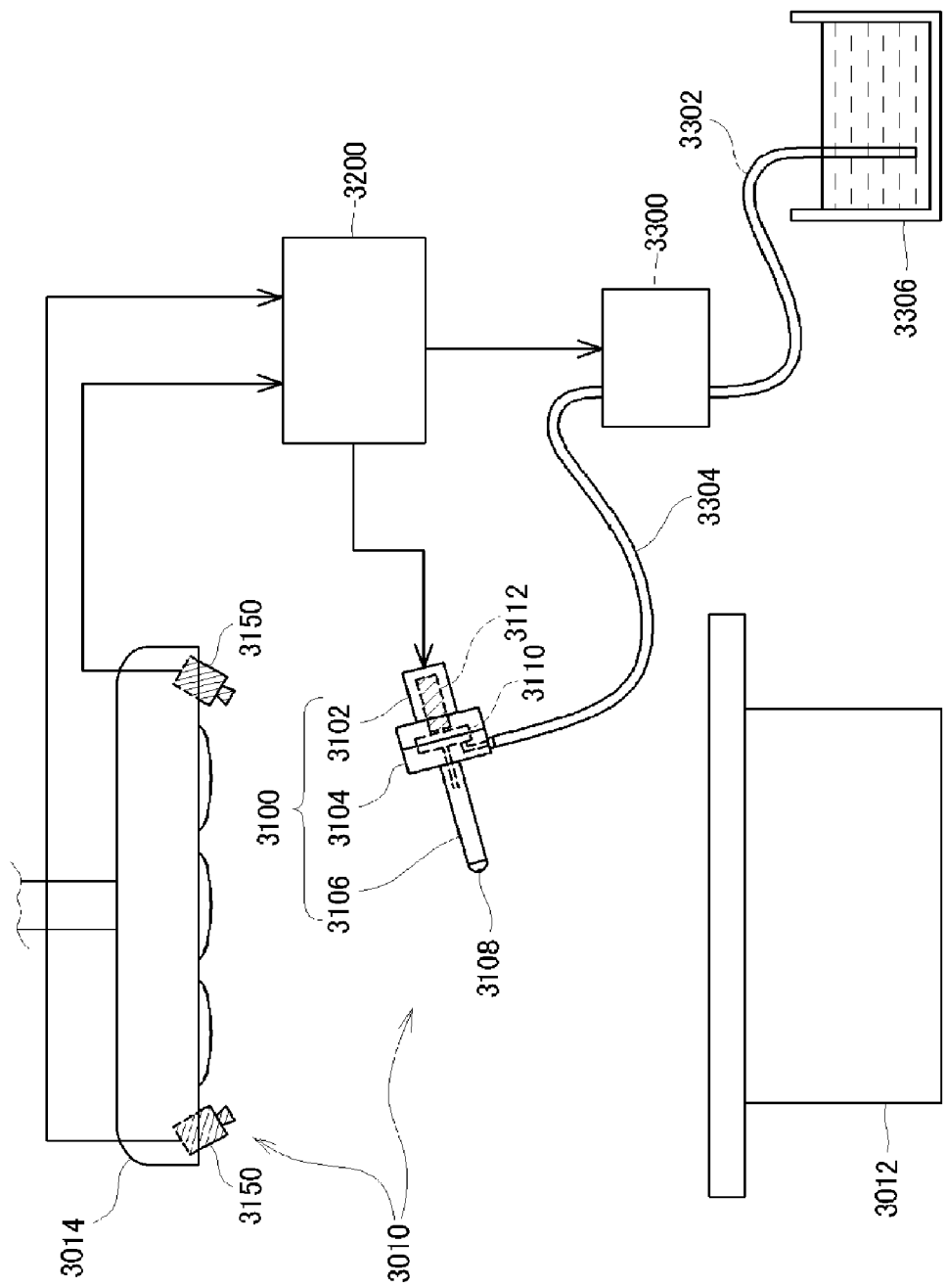
FIG. 21 is an explanatory diagram showing a rough configuration of a medical apparatus according to a third embodiment.

A third embodiment of the invention is explained. FIG. 21 is an explanatory diagram showing a rough configuration of a medical apparatus 3010 according to this embodiment. The medical apparatus 3010 shown in the figure is used for a surgical operation method for incising or excising a biological tissue by ejecting liquid such as water or saline to the biological tissue.

As shown in the figure, the medical apparatus 3010 in this embodiment includes an applicator 3100 held by an operator by hand and operated to eject liquid, a liquid supply unit 3300 configured to supply the liquid to the applicator 3100, a liquid container 3306 configured to store the liquid to be ejected, a camera 3150 configured to photograph a state in which the applicator 3100 is operated, and a control unit 3200 configured to control the operation of the applicator 3100 and the liquid supply unit 3300.

The applicator 3100 includes a first case 3102, a second case 3104 attached to the first case 3102, a liquid ejection pipe 3106 provided to project from the second case 3104 to the opposite side of the first case 3102, and a nozzle 3108 provided at the distal end of the liquid ejection pipe 3106. A liquid chamber 3110 is formed on a mating face of the first case 3102 and the second case 3104. A liquid supply unit 3300 is connected to the liquid chamber 3110 via a second connection tube 3304. The liquid supply unit 3300 is connected to the liquid container 3306 via a first connection tube 3302. When the liquid supply unit 3300 is actuated, the liquid in the liquid container 3306 is supplied to the liquid chamber 3110. The first case 3102 and the second case 3104 in this embodiment correspond to the "liquid ejecting unit" in the invention.

A laminated piezoelectric element 3112 is housed in the first case 3102. As explained in detail below, when a driving voltage is applied to the piezoelectric element 3112 from the control unit 3200, the liquid in the liquid chamber 3110 is ejected from the nozzle 3108 in a pulse-like manner. The piezoelectric element 3112 in this embodiment corresponds to the "pulsation generating unit" in the invention.

Cameras 3150 are provided in an illuminator 3014 that illuminates an operating table 3012 from above. The cameras 3150 are provided in a plurality of places (two places in this embodiment) of the illuminator 3014. The respective cameras 3150 photograph, at every predetermined time interval, a state in the vicinity of a surgical site where the applicator 3100 is operated. An image photographed by the camera 3150 is input to the control unit 3200. As explained in detail below, the control unit 3200 detects moving speed of the nozzle 3108 of the applicator 3100 on the basis of an analysis result of the photographed image. The control unit 3200 controls, according to the moving speed of the nozzle 3108, the number of times the driving voltage is applied to the piezoelectric element 3112 per unit time (a driving frequency). The camera 3150 in this embodiment corresponds to the "photographing unit" in the invention. The control unit 3200 in this embodiment corresponds to the "pulsation-generation control unit" and the "moving-speed detecting unit" in the invention.

FIGS. 22A and 22B are explanatory diagrams showing detailed structure of the applicator 3100. An exploded sectional view of the applicator 3100 is shown in FIG. 22A. A sectional view after assembly is shown in FIG. 22B. In the first case 3102, a large circular shallow recess 3102c is formed substantially in the center of a face mating with the second case 3104. A through-hole 3102h circular in section is formed in the center position of the recess 3102c to pierce through the first case 3102.

A thin diaphragm 3114 of metal is provided in the bottom of the recess 3102c to close the through-hole 3102h. The peripheral edge portion of the diaphragm 3114 is hermetically fixedly attached to the bottom of the recess 3102c by a method such as brazing or diffusion bonding. A reinforcing plate 3120 of metal formed in an annular shape is loosely fit in the recess 3102c on the diaphragm 3114. The piezoelectric element 3112 is housed in the through-hole 3102h closed by the diaphragm 3114. On the rear side of the piezoelectric element 3112, the through-hole 3102h is closed by a bottom plate 3101 of metal formed in a disk shape. A disk-shaped shim 3116 of metal is provided between the piezoelectric element 3112 and the diaphragm 3114.

In the second case 3104, a circular shallow recess 3104c is formed on a face on a side mating with the first case 3102. The inner diameter of the recess 3104c is set to substantially the same size as the inner diameter of the reinforcing plate 3120 fit in the first case 3102. When the first case 3102 is assembled to the second case 3104, a substantially disk-shaped liquid chamber 3110 is formed by the diaphragm 3114 and the inner circumferential surface of the reinforcing plate 3120 provided on the first case 3102 side and the recess 3104c provided in the second case 3104. In the second case 3104, a supply passage 3104i for supplying the liquid from a side of the second case 3104 to the liquid chamber 3110 is provided. An ejection passage 3104o, through which the liquid pressurized in the liquid chamber 3110 passes, pierces the center position of the recess 3104c. In an opening portion of the ejection passage 3104o, the liquid ejection pipe 3106 is inserted and attached in the inner diameter portion thereof. The nozzle 3108 is formed at the distal end of the liquid ejection pipe 3106.

In the applicator 3100 having such a configuration, when a voltage is applied to the piezoelectric element 3112 to expand the piezoelectric element 3112, the diaphragm 3114 is deformed and the capacity of the liquid chamber 3110 decreases. When the voltage applied to the piezoelectric element 3112 is released, the diaphragm 3114 is restored from the deformation and the capacity of the liquid chamber 3110 returns to the original capacity. Therefore, when the driving voltage is applied to the piezoelectric element 3112 and the capacity of the liquid chamber 3110 is reduced while the liquid is supplied to the liquid chamber 3110, the liquid in the liquid chamber 3110 is pressurized and ejected from the nozzle 3108 in a pulse-like manner. When the voltage applied to the piezoelectric element 3112 is released and the capacity of the liquid chamber 3110 is returned to the original capacity, the liquid equivalent to the ejected amount is supplied into the liquid chamber 3110. When the driving voltage is applied to the piezoelectric element 3112 again in this state, the capacity of the liquid chamber 3110 decreases and the liquid in the liquid chamber 3110 is ejected from the nozzle 3108 in a pulse-like manner. Therefore, the driving voltage is applied to the piezoelectric element 3112 at a predetermined driving frequency, whereby the liquid in the liquid chamber 3110 pulsates and the pulse-like liquid is ejected from the nozzle 3108 at a fixed period. The pulse-like ejection of the liquid means ejection of the liquid at a regularly or irregularly fluctuating flow rate or moving speed of the liquid to be ejected. Examples of the pulse-like ejection include intermittent ejection for repeating ejection and non-ejection of the liquid. However, the flow rate or the moving speed of the liquid to be ejected only has to regularly or irregularly fluctuate. The pulse-like ejection does not always need to be the intermittent ejection.

Figure 23:
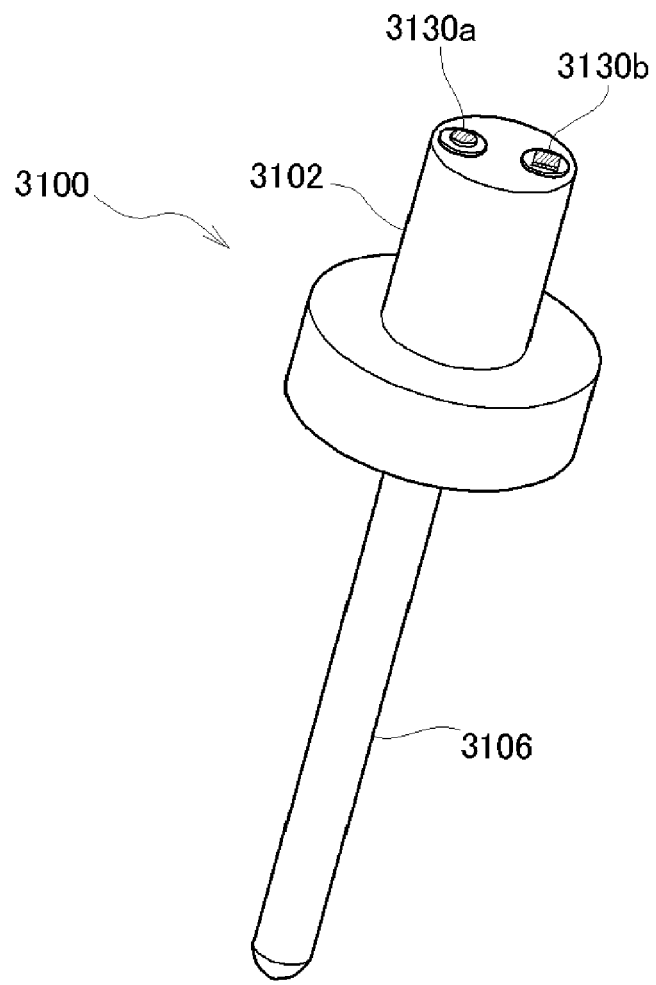
FIG. 23 is an explanatory diagram showing an external appearance of the applicator in the third embodiment.

FIG. 23 is a perspective view showing the external appearance of the applicator 3100. As shown in the figure, in the applicator 3100 in this embodiment, markers 3130 (mark members) are stuck to a plurality of places (two places in this embodiment) on the surface of the applicator 3100. In the applicator 3100 in this embodiment, markers 3130a and 3130b are stuck to positions at an end in an upper part of the first case 3102 in the figure. However, positions to which the markers 3130a and 3130b are stuck are not limited to these positions. The markers 3130a and 3130b only have to be provided in any position on the surface of the applicator 3100.

In the medical apparatus 3010 having the configuration explained above, a biological tissue is incised or excised by moving the position of the nozzle 3108 while ejecting the pulse-like liquid from the nozzle 3108 of the applicator 3100 at a fixed period. When the biological tissue is incised or excised using the medical apparatus 3010, depth of excision of the biological tissue (excision depth) changes according to speed at which the operator moves the position of the nozzle 3108. A reason for the change is as explained below.

Figure 24A:
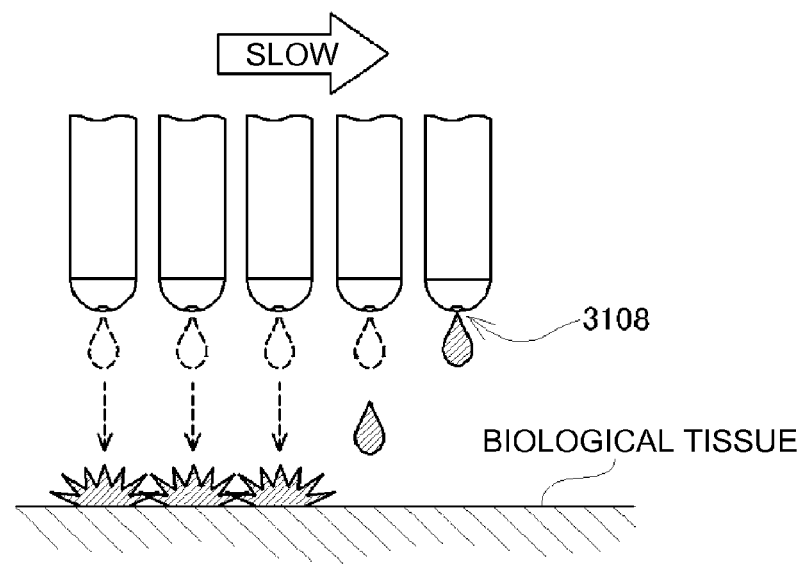
FIGS. 24A and 24B are explanatory diagrams showing a mechanism in which excision depth of a biological tissue changes according to the moving speed of a nozzle in the third embodiment.
Figure 24B:
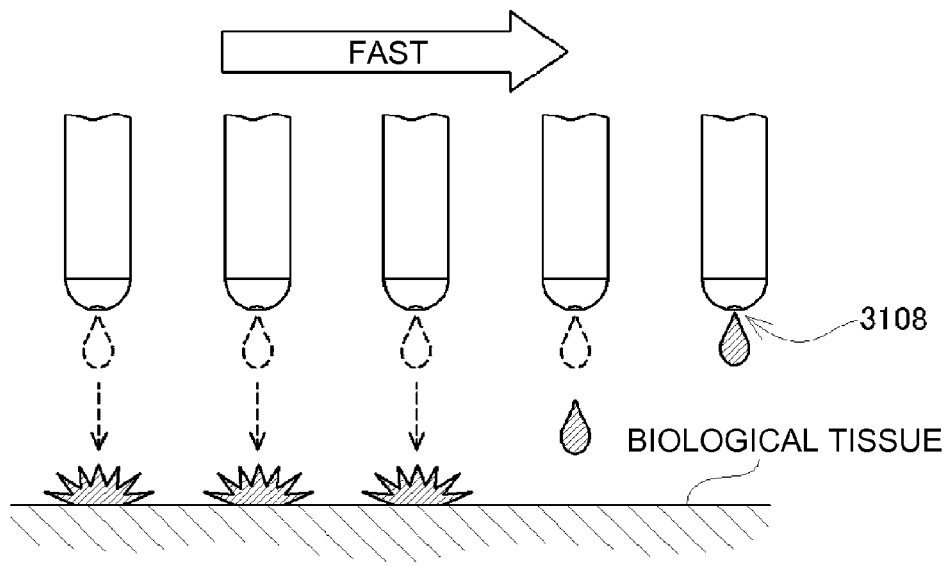

FIGS. 24A and 24B are explanatory diagrams showing a mechanism in which the excision depth of the biological tissue changes according to the moving speed of the nozzle 3108. In FIG. 24A, the moving speed of the nozzle 3108 is low. In FIG. 24B, the moving speed of the nozzle 3108 is high. If the driving frequency for applying the driving voltage to the piezoelectric element 3112 is the same, the number of times the liquid is ejected from the nozzle 3108 in a pulse-like manner per unit time is the same. Therefore, for example, as shown in FIG. 24B, when the moving speed of the nozzle 3108 increases, the liquid is sparsely ejected (the number of times the liquid is ejected per unit length decreases). As a result, the excision depth of the biological tissue is small in FIG. 24B compared with FIG. 24A. On the other hand, in this embodiment, since the driving frequency is increased when the moving speed of the nozzle 3108 increases, it is possible to keep the excision depth at the same depth. The same applies when the moving speed of the nozzle 3108 decreases. That is, when the moving speed of the nozzle 3108 decreases, since the liquid is densely ejected (the number of times the liquid is ejected per unit length increases), the excision depth of the biological tissue increases. On the other hand, in this embodiment, since the driving frequency is reduced when the moving speed of the nozzle 3108 decreases, it is possible to keep the excision depth.

When the excision depth of the biological tissue changes according to the speed for moving the nozzle 3108 as explained above, it is difficult to excise the biological tissue at stable depth. When the operator does not remember that the operator changed the moving speed of the nozzle 3108, the operator undesirably misunderstands that the sharpness of the medical apparatus 3010 has changed. Therefore, in the medical apparatus 3010 in this embodiment, the driving of the piezoelectric element 3112 is controlled as explained below, whereby the excision depth of the biological tissue is prevented from changing according to the moving speed of the nozzle 3108.

E-2. Driving Control Processing in the Third Embodiment

Figure 25:
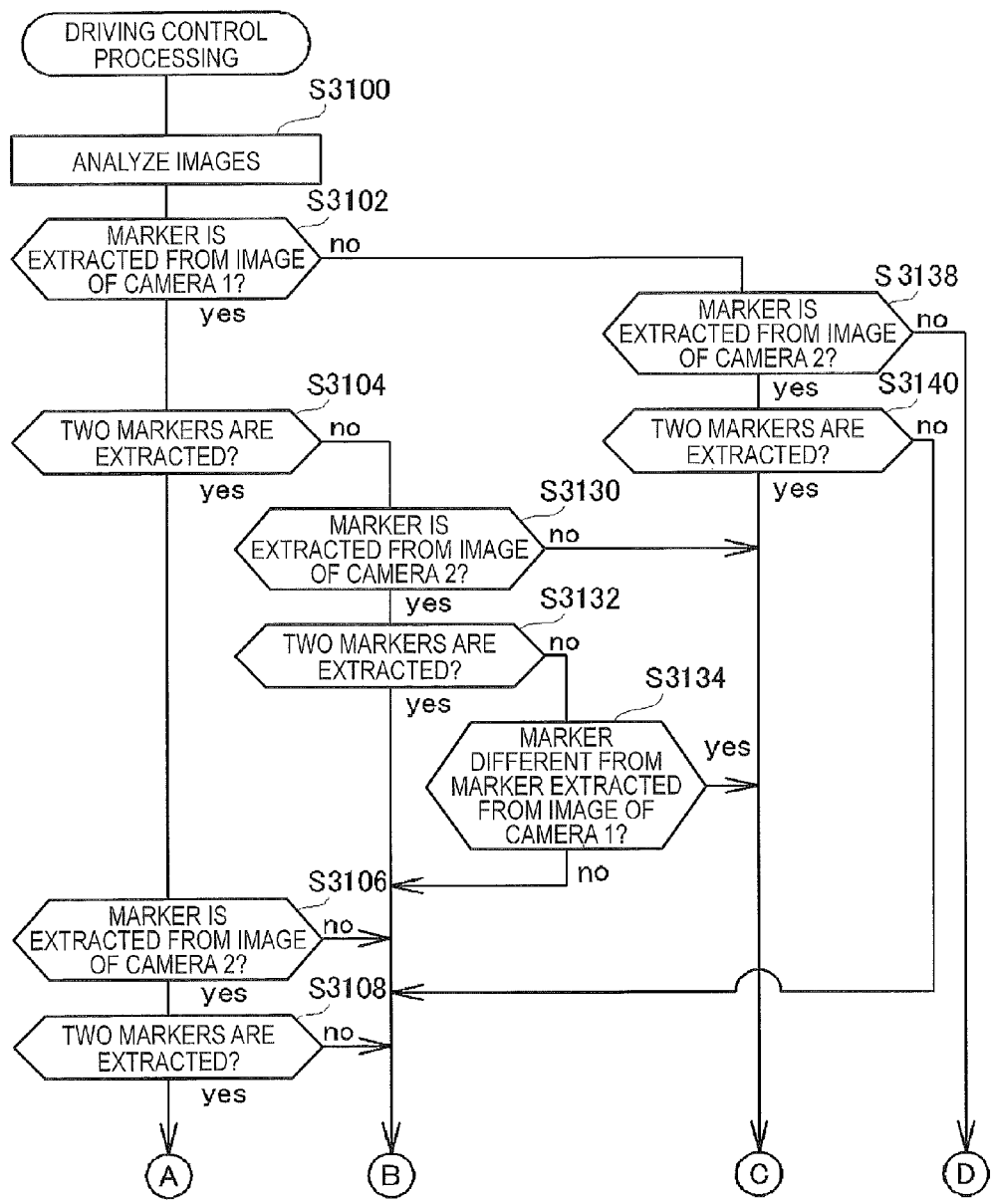
FIG. 25 is a former half of a flowchart of driving control processing performed by a control unit to control driving of a piezoelectric element in the third embodiment.
Figure 26:
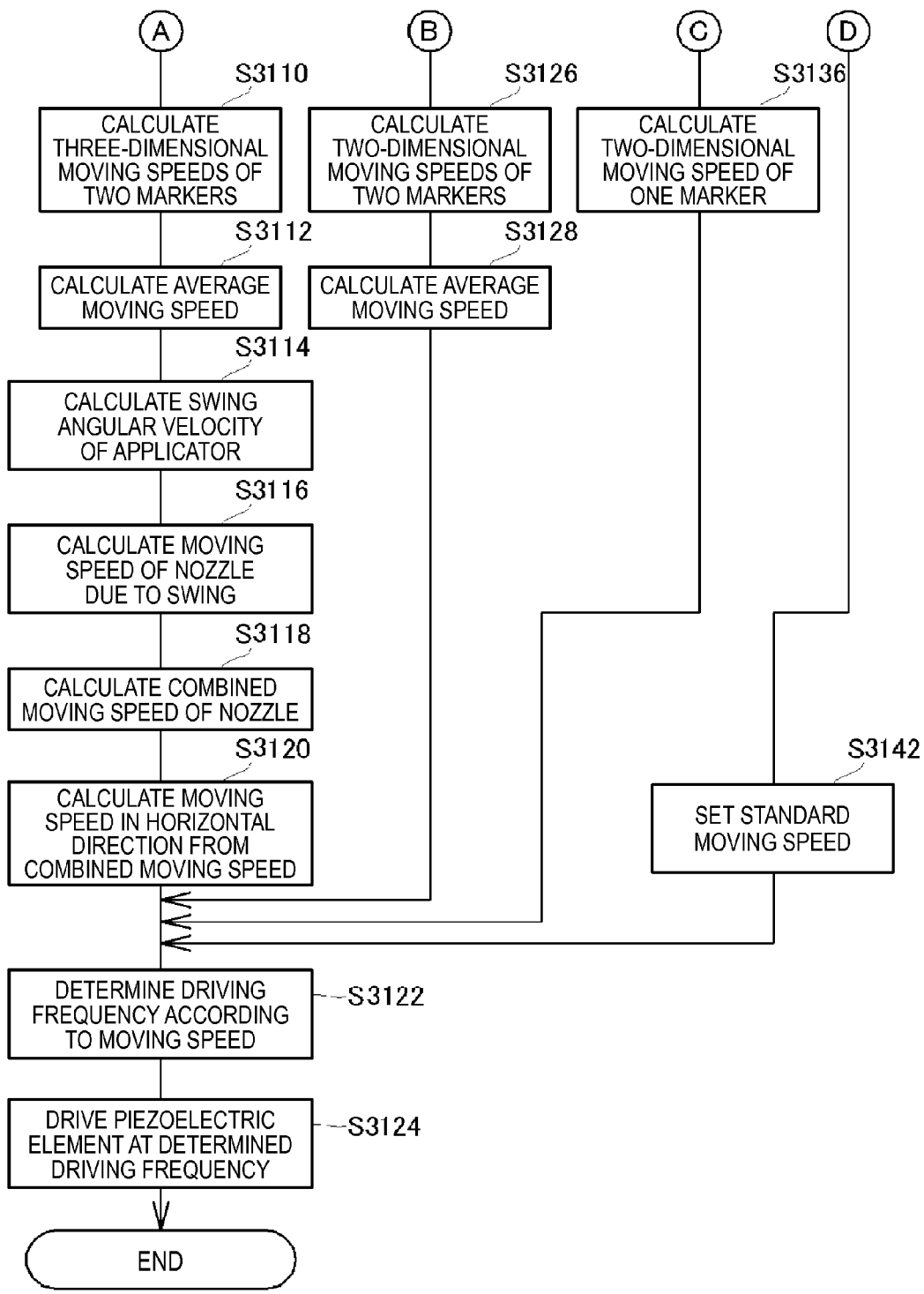
FIG. 26 is a latter half of the flowchart of the driving control processing performed by the control unit to control driving of the piezoelectric element in the third embodiment.
Figure 28:
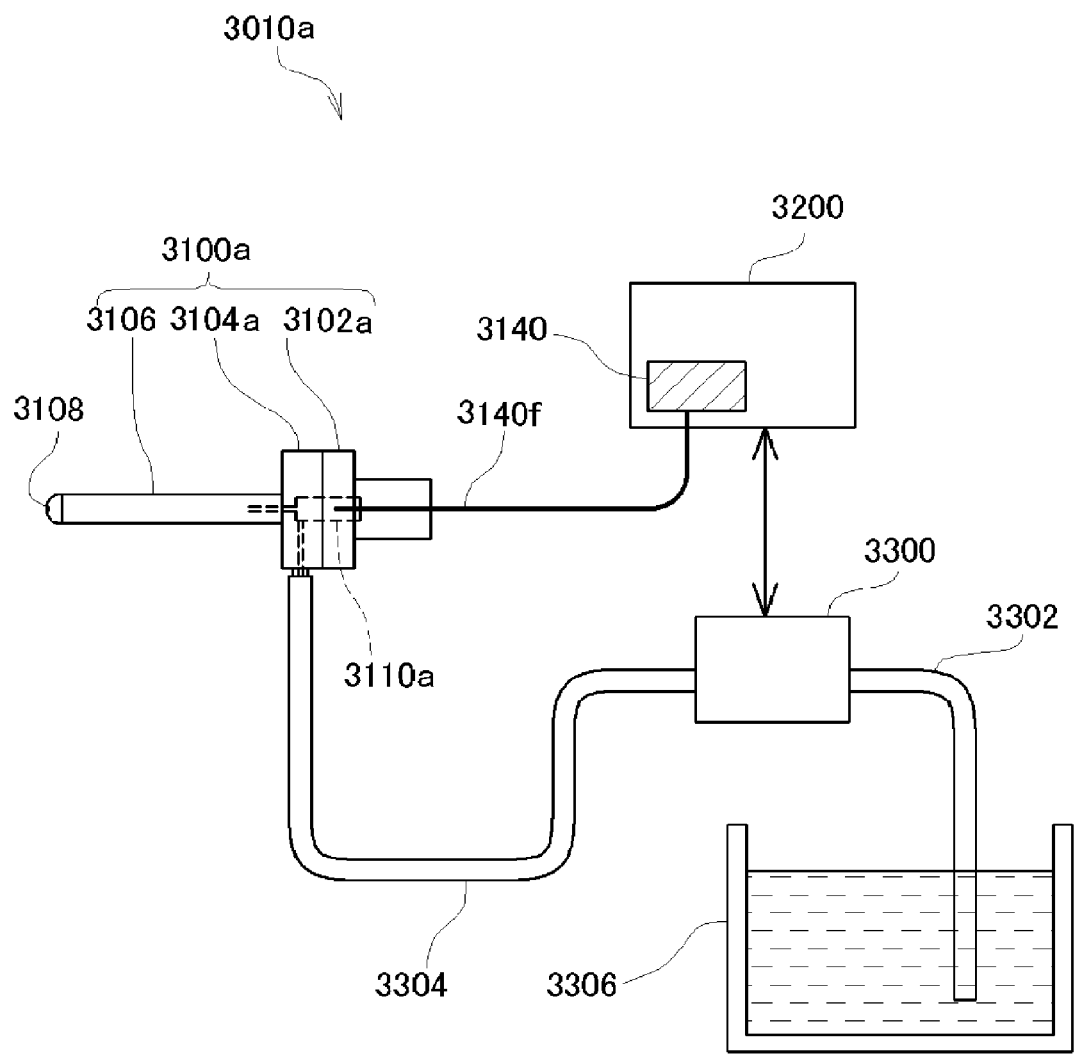
FIG. 28 is an explanatory diagram of a first modification in which liquid is ejected using a laser in the third embodiment.

FIGS. 25 and 26 are a flowchart of driving control processing performed by the control unit 3200 in this embodiment to control driving of the piezoelectric element 3112. In FIG. 25, a former half of the flowchart of the driving control processing in this embodiment is shown. In FIG. 26, a latter half of the flowchart of the driving control processing in this embodiment is shown. As explained above, the two cameras 3150 are provided in the medical apparatus 3010 in this embodiment (see FIG. 21). Images are photographed by the cameras 3150 at every predetermined time interval. The images are input to the control unit 3200. The control unit 3200 performs processing explained below every time images are input from the cameras 3150. In the following explanation, one camera 3150 of the two cameras 3150 is referred to as camera 1 and the other camera 3150 is referred to as camera 2.

As shown in FIG. 25, upon starting the driving control processing, first, the control unit 3200 analyzes input images (step S3100). The control unit 3200 determines whether the marker 3130 (see FIG. 23) of the applicator 3100 has been able to be extracted out of the image of the camera 1 as a result of the analysis (step S3102). When the marker 3130 has been extracted out of the image of the camera 1 (yes in step S3102), the control unit 3200 determines whether the two markers 3130a and 3130b have been extracted out of the image (step S3104). When the two markers 3130a and 3130b have been extracted out of the image of the camera 1 (yes in step S3104), the control unit 3200 performs the same determination concerning the camera 2. That is, the control unit 3200 determines whether the marker 3130 of the applicator 3100 has been able to be extracted out of the image of the camera 2 (step S3106). When the marker 3130 has been extracted out of the image of the camera 2 (yes in step S3106), the control unit 3200 determines whether the two markers 3130a and 3130b have been extracted out of the image (step S3108). When the two markers 3130a and 3130b have been extracted out of the image of the camera 2 as well (yes in step S3108), the control unit 3200 calculates three-dimensional moving speed of the two markers 3130a and 3130b (step S3110 in FIG. 26).

When the two markers 3130a and 3130b have been extracted out of the respective images of the camera 1 and the camera 2 (yes in steps S3102 to S3108), both the markers 3130a and 3130b have been photographed by the two cameras. Therefore, respective three-dimensional positions of the marker 3130a and 3130b are acquired. Since the camera 1 and the camera 2 photograph images at every very short time interval, if three-dimensional positions of the marker 3130a and the marker 3130b are acquired by the photographing of this time, three-dimensional positions of the marker 3130a and the marker 3130b are acquired by the photographing of the last time. The three-dimensional positions of the marker 3130a and the marker 3130b acquired during the photographing of the last time are stored in a RAM of the control unit 3200. Therefore, the control unit 3200 calculates distances between the positions of the markers 3130a and 3130b acquired last time and the positions of the markers 3130a and 3130b acquired this time and divides the distances by a time interval of the photographing to thereby calculate three-dimensional moving speeds of the markers 3130a and 3130b (step S3110).

After calculating the three-dimensional moving speeds of the markers 3130a and 3130b (step S3110), the control unit 3200 calculates moving speed of the nozzle 3108 by performing a series of processing explained below. First, the control unit 3200 calculates an average value (average moving speed) of the three-dimensional moving speeds of the two markers 3130a and 3130b (step S3112). Subsequently, the control unit 3200 calculates, on the basis of the three-dimensional moving speeds of the two markers 3130a and 3130b, an angular velocity of a motion of the applicator 3100 whirling with respect to the axis direction (hereinafter referred to as swinging motion) (step S3114). Further, the control unit 3200 multiplies the calculated angular velocity of the swinging motion with a span of the applicator 3100 (length from a position of the applicator 3100 gripped by the operator to the tip of the nozzle 3108) to thereby calculate moving speed of the nozzle 3108 due to the swinging motion (step S3116). The control unit 3200 adds the moving speed of the nozzle 3108 due to the swinging motion to the average moving speed of the markers 3130 to thereby calculate combined moving speed of the nozzle 3108 (step S3118).

After calculating the combined moving speed of the nozzle 3108 (step S3118), the control unit 3200 calculates moving speed in the horizontal direction of the nozzle 3108 from the combined moving speed (step S3120). The control unit 3200 determines a driving frequency of the piezoelectric element 3112 according to the calculated moving speed (step S3122). The control unit 3200 determines the driving frequency corresponding to the moving speed of the nozzle 3108 by referring to a table stored in advance in a ROM of the control unit 3200.

FIG. 27 is an explanatory diagram conceptually showing a table in which driving frequencies corresponding to moving speeds of the nozzle 3108 are stored. As shown in the figure, in a range until the moving speed of the nozzle 3108 reaches upper limit speed, the driving frequency is set to a value proportional to the moving speed of the nozzle 3108. Therefore, the number of pulses (the number of times of ejection of the liquid) per unit length of the nozzle 3108 is fixed irrespective of the moving speed of the nozzle 3108. After the moving speed of the nozzle 3108 reaches the upper limit speed, the driving frequency is retained at an upper limit frequency. Therefore, a situation is avoided in which the value of the driving frequency is excessively large and the supply of the liquid to the liquid chamber 3110 by the liquid supply unit 3300 does not catch up with a necessary supply amount and, as a result, the liquid cannot be ejected from the nozzle 3108. In FIG. 27, the moving speed and the driving frequency are explained as being completely proportional to each other until the moving speed of the nozzle 3108 reaches the upper limit speed. However, the moving speed and the driving frequency only have to be roughly proportional to each other. It is also possible to slightly increase or decrease the driving frequency from a value proportional to the moving speed such that a more desirable result is obtained.

In the driving control processing in this embodiment, the control unit 3200 determines a driving frequency of the piezoelectric element 3112 by referring to such a table (step S3122 in FIG. 26). The control unit 3200 applies the driving voltage to the piezoelectric element 3112 at the determined driving frequency to thereby drive the piezoelectric element 3112 (step S3124).

In the above explanation, the two markers 3130a and 3130b are extracted out of the image of the camera 1 and the two markers 3130a and 3130b are extracted out of the image of the camera 2 as well (yes in steps S3102 to S3108 in FIG. 25). On the other hand, in some case, the two markers 3130a and 3130b are extracted out of the image of the camera 1 (yes in step S3102 and yes in step S3104) and only one of the two markers 3130a and 3130b is extracted out of the image of the camera 2 (yes in step S3106 and no in step S3108). In this case, a three-dimensional position is acquired concerning the marker 3130 extracted out of both the images of the camera 1 and the camera 2 and two-dimensional positions are acquired concerning the marker 3130 extracted out of only the image of the camera 1.

Even the three-dimensional position of only the one marker 3130 is acquired, a swing angular velocity of the applicator 3100 cannot be calculated. Therefore, moving speed of the nozzle due to a swing cannot be calculated. In such a case (no in step S3108), the control unit 3200 calculates moving speed of the nozzle 3108 without taking into account the moving speed of the nozzle 3108 due to a swing. First, the control unit 3200 calculates two-dimensional moving speeds of the two markers 3130a and 3130b respectively on the basis of the two-dimensional positions of the markers 3130a and 3130b (step S3126 in FIG. 26). At this point, concerning the marker 3130, the three-dimensional position of which is acquired, the control unit 3200 calculates moving speed using components of two-dimensional positions in information indicating the three-dimensional position. Subsequently, the control unit 3200 calculates an average value of the two-dimensional moving speeds of the two markers 3130a and 3130b (step S3128). The control unit 3200 regards the calculated value (the average value of the two-dimensional moving speeds of the two markers 3130a and 3130b) as the moving speed in the horizontal direction of the nozzle 3108 and determines a driving frequency corresponding to the moving speed (step S3122). The control unit 3200 applies the driving voltage to the piezoelectric element 3112 at the determined driving frequency to thereby drive the piezoelectric element 3112 (step S3124).

In some case, the two markers 3130a and 3130b are extracted out of the image of the camera 1 (yes in step S3102 and yes in step S3104) and the markers 3130a and 3130b are not extracted out of the image of the camera 2 (no in step S3106). In this case, two-dimensional positions of the marker 3130a and the marker 3130b are acquired from the image of the camera 1. Then, the control unit 3200 calculates two-dimensional moving speeds of the two markers 3130a and 3130b respectively on the basis of the two-dimensional positions of the markers 3130a and 3130b (step S3126 in FIG. 26). Thereafter, as in the case explained above, the control unit 3200 calculates an average value of the two-dimensional moving speeds of the two markers 3130a and 3130b (step S3128), determines a driving frequency according to the average value (equivalent to the moving speed in the horizontal direction of the nozzle 3108) (step S3122), and drives the piezoelectric element 3112 at the determined driving frequency (step S3124).

In some case, one of the two markers 3130a and 3130b is extracted out of the image of the camera 1 (yes in step S3102 and no in step S3104) and the two markers 3130a and 3130b are extracted out of the image of the camera 2 (yes in step S3130 and yes in step S3132). In this case, as in the case in which the two markers 3130a and 3130b are extracted out of the image of the camera 1 (yes in step S3102 and yes in step S3104) and only one of the two markers 3130a and 3130b is extracted out of the image of the camera 2 (yes in step S3106 and no in step S3108), a three-dimensional position of one marker 3130 is acquired and a two-dimensional position of the other markers 3130 is acquired. Therefore, the control unit 3200 calculates moving speed of the nozzle 3108 in the same manner. That is, the control unit 3200 calculates two-dimensional moving speeds of the two markers 3130a and 3130b on the basis of the two-dimensional positions of the markers 3130a and 3130b (step S3126 in FIG. 26), calculates an average value of the two-dimensional moving speeds of the two markers 3130a and 3130b (step S3128), and drives the piezoelectric element 3112 at a driving frequency corresponding to the average value (equivalent to the moving speed in the horizontal direction of the nozzle 3108) (step S3122 and step S3124).

In some case, one of the two markers 3130a and 3130b is extracted out of the image of the camera 1 (yes in step S3102 and no in step S3104), one of the two markers 3130a and 3130b is extracted out of the image of the camera 2 as well (yes in step S3130 and no in step S3132), and the marker 3130 in the image of the camera 1 and the marker 3130 in the image of the camera 2 are different (yes in step S3134). In this case, two-dimensional positions of the two markers 3130a and 3130b are acquired from the images of the camera 1 and the camera 2. Then, the control unit 3200 calculates two-dimensional moving speeds of the two markers 3130a and 3130b respectively on the basis of the two-dimensional positions of the markers 3130a and 3130b (step S3126 in FIG. 26), calculates an average value of the two-dimensional moving speeds of the two markers 3130a and 3130b (step S3128), and drives the piezoelectric element 3112 at a driving frequency corresponding to the average value (step S3122 and step S3124).

In some case, one of the two markers 3130a and 3130b is extracted out of the image of the camera 1 (yes in step S3102 and no in step S3104), one of the two markers 3130a and 3130b is extracted out of the image of the camera 2 as well (yes in step S3130 and no in step S3132), and the marker 3130 in the image of the camera 1 and the marker 3130 in the image of the camera 2 are the same (no in step S3134). In this case, a three-dimensional position of the one marker 3130 is acquired. As explained above, even if only the three-dimensional position of the one marker 3130 is acquired, moving speed due to the swing of the nozzle 3108 cannot be calculated. Therefore, the control unit 3200 calculates two-dimensional moving speed of the one marker 3130 on the basis of components of two-dimensional positions in information indicating the three-dimensional position of the one marker 3130 (step S3136 in FIG. 26). The control unit 3200 regards a calculated value (the two-dimensional moving speed of the one marker 3130) as the moving speed in the horizontal direction of the nozzle 3108 and determines a driving frequency according to the moving speed (step S3122). The control unit 3200 applies the driving voltage at the determined driving frequency to thereby drive the piezoelectric element 3112 (step S3124).

In some case, one of the two markers 3130a and 3130b is extracted out of the image of the camera 1 (yes in step S3102 and no in step S3104) and the marker 3130 is not extracted out of the image of the camera 2 (no in step S3130). In this case, a two-dimensional position of the one marker 3130 is acquired from the image of the camera 1. Then, the control unit 3200 calculates two-dimensional moving speed of the one marker 3130 on the basis of the two-dimensional position of the one marker 3130 (step S3136 in FIG. 26) and drives the piezoelectric element 3112 at a driving frequency corresponding to the moving speed (equivalent to the moving speed in the horizontal direction of the nozzle 3108) (step S3122 and step S3124).

In some case, the markers 3130a and 3130b are not extracted out of the image of the camera 1 (no in step S3102) and the two markers 3130a and 3130b are extracted out of the image of the camera 2 (yes in step S3138 and yes in step S3140). In this case, two-dimensional positions of the two markers 3130a and 3130b are acquired from the image of the camera 2. Therefore, the control unit 3200 calculates two-dimensional moving speeds of the two markers 3130a and 3130b respectively on the basis of the two-dimensional positions of the markers 3130a and 3130b (step S3126 in FIG. 26). Thereafter, as in the case explained above, the control unit 3200 calculates an average value of the two-dimensional moving speeds of the two markers 3130a and 3130b (step S3128) and drives the piezoelectric elements 3112 at a driving frequency corresponding to the average value (steps S3122 and step S3124).

In some case, the markers 3130a and 3130b are not extracted out of the image of the camera 1 (no in step S3102) and one of the two markers 3130a and 3130b is extracted out of the image of the camera 2 (yes in step S3138 and no in step S3140). In this case, a two-dimensional position of the one marker 3130 is acquired from the image of the camera 2. Therefore, the control unit 3200 calculates two-dimensional moving speed of the one marker 3130 on the basis of the two-dimensional position of the one marker 3130 (step S3136 in FIG. 26). Thereafter, as in the case explained above, the control unit 3200 drives the piezoelectric element 3112 at a driving frequency corresponding to the two-dimensional moving speed of the one marker 3130 (step S3122 and step S3124).

In some case, the markers 3130a and 3130b are not extracted out of the image of the camera 1 (no in step S3102) and the markers 3130a and 3130b are not extracted out of the image of the camera 2 either (no in step S3138). In this case, both two-dimensional positions and three-dimensional positions of the markers 3130a and 3130b cannot be acquired. Therefore, moving speed (moving speed in the horizontal direction) of the nozzle 3108 cannot be calculated. In such a case (no in step S3138), the control unit 3200 sets standard moving speed as the moving speed in the horizontal direction of the nozzle 3108 (step S3142). The control unit 3200 determines a driving frequency corresponding to the set standard moving speed (step S3122) and drives the piezoelectric element 3112 at the determined driving frequency (step S3124).

As explained above, in the driving control processing in this embodiment, the control unit 3200 calculates, every time images are input from the cameras 3150, moving speed of the nozzle 3108 on the basis of the input images of the applicator 3100 and drives the piezoelectric element 3112 at a driving frequency corresponding to the moving speed.

By performing such control, in the medical apparatus 3010 in this embodiment, it is possible to increase the driving frequency of the piezoelectric element 3112 when the moving speed of the nozzle 3108 increases and reduce the driving frequency when the moving speed of the nozzle 3108 decreases. As a result, even if the moving speed of the nozzle 3108 changes, it is possible to fix the number of times of ejection of the liquid per unit length of the nozzle 3108. Therefore, it is possible to excise the biological tissue at stable excision depth.

As explained above, in the medical apparatus 3010 in this embodiment, three-dimensional moving speeds of the markers 3130 provided in the plurality of places (the two places in this embodiment) of the applicator 3100 are respectively calculated, whereby moving speed (combined moving speed) of the nozzle 3108 is calculated taking into account not only the translating motion of the applicator 3100 but also the swinging motion of the applicator 3100. Consequently, it is possible to more accurately calculate moving speed of the nozzle 3108. As a result, it is possible to more surely realize excision of the biological tissue at stable excision depth by driving the piezoelectric element 3112 at a driving frequency corresponding to the calculated moving speed of the nozzle 3108.

F. Modifications in the Third Embodiment

Several modifications are conceivable concerning the medical apparatus 3010 in the third embodiment. The modifications are briefly explained below.

F-1. First Modification in the Third Embodiment

In the explanation in the third embodiment, the liquid is ejected from the nozzle 3108 in a pulse-like manner by applying the driving voltage to the piezoelectric element 3112 and reducing the capacity of the liquid chamber 3110. However, the liquid may be ejected from the nozzle 3108 in a pulse-like manner by irradiating laser light in a pulse-like manner.

In an example shown in FIG. 27, a laser oscillator 3140 is mounted in the control unit 3200. Laser light from the laser oscillator 3140 is guided to the liquid chamber 3110 by an optical fiber cable 3140f. In an applicator 3100a in this modification, the shape of a liquid chamber 3110a on the inside of a first case 3102a and a second case 3104a is different from the shape in the third embodiment. The terminal end of the optical fiber cable 3140f is arranged on the inside of the liquid chamber 3110a. Ina medical apparatus 3010a in the first modification, it is possible to emit a pulse-like laser from the laser oscillator 3140 and instantaneously boil the liquid on which the laser is irradiated in the liquid chamber 3110a. As a result, the liquid in the liquid chamber 3110a is instantaneously boiled by laser light irradiated from the terminal end of the optical fiber cable 3140f. As a result, the liquid is pressurized. It is possible to eject the liquid from the nozzle 3108 in a pulse-like manner.

F-2. Second Modification in the Third Embodiment

Figure 29:
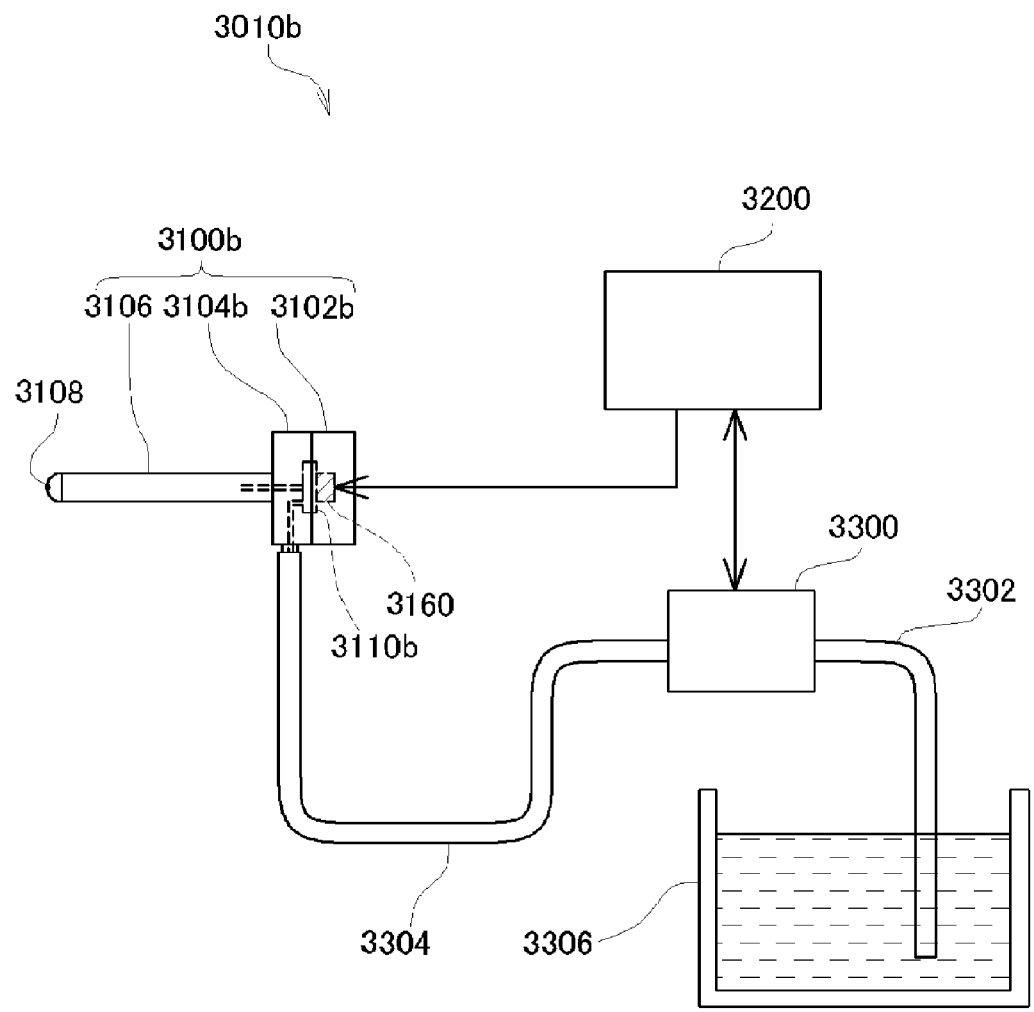
FIG. 29 is an explanatory diagram of a second modification in which liquid is ejected using a heater in the third embodiment.

A configuration in a second modification of the third embodiment is shown in FIG. 29. In a medical apparatus 3010b in the second modification, as shown in the figure, a heater 3160 is provided in a liquid chamber 3110b of an applicator 3100b of the medial apparatus 3010b. A first case 3102b and a second case 3104b of the applicator 3100b are shaped to be capable of incorporating the heater 3160. The heater 3160 has an ability of generating heat when energized and reaching temperature for boiling the liquid in contact with the heater 3160 in a short time (substantially instantaneously).

In an example shown in FIG. 29, the heater 3160 is incorporated in a part of the liquid chamber 3110b. An electric current can be supplied in a pulse-like manner from the control unit 3200 to the heater 3160. If the pulse-like electric current is fed to the heater 3160, the liquid in a portion in contact with the heater 3160 in the liquid chamber 3110*b* can be instantaneously boiled. Therefore, it is possible to pressurize the liquid in the liquid chamber 3110*b*. As a result, it is possible to eject the liquid in a pulse-like manner from the nozzle 3108.

The invention is explained above with reference to the third embodiment and the modifications thereof. However, the invention is not limited to the embodiment and the modifications and can be carried out in various forms without departing from the spirit of the invention. For example, in the explanation of the medical apparatus 3010 in this embodiment, the applicator 3100 is photographed by the two cameras 3150. However, the applicator 3100 may be photographed by a larger number of cameras 3150 (three or more cameras). Consequently, it is possible to highly accurately detect the positions of the markers 3130 by photographing the applicator 3100 from a large number of directions (three or more directions). As a result, it is possible to accurately detect moving speed of the nozzle. Therefore, it is possible to set a driving frequency of the piezoelectric element 3112 to an appropriate driving frequency corresponding to the moving speed of the nozzle 3108.

In the explanation of the medical apparatus 3010 in the embodiment, the cameras 3150 are provided in the illuminator 3014. However, the cameras 3150 may be provided in another form as long as the cameras 3150 can photograph the vicinity of a surgical site where the applicator 3100 is operated. Therefore, for example, a tall carriage may be arranged around the operating table 3012, the cameras 3150 may be fixed to an upper part of the carriage, and the applicator 3100 may be photographed by the cameras 3150.

The embodiments of the invention and the modifications of the embodiments are explained above. However, the invention is limited to the embodiments and the modifications by no means. The technical scope of the invention is interpreted according to the technical idea and the spirit of the invention described in the appended claims below.

What is claimed is:

1. A medical apparatus that ejects liquid from a nozzle provided at a distal end of a liquid ejection pipe, the medical apparatus comprising:
   a pulsation generating unit configured to change a capacity of a liquid chamber connected to the liquid ejection pipe according to displacement of a piezoelectric element and generate pulsation in the liquid;
   a liquid supplying unit configured to supply the liquid to the liquid chamber;
   a moving-speed detecting unit configured to detect the moving speed of the nozzle with respect to a liquid ejection target which is external to the nozzle; and
   a pulsation-generation control unit which controls the pulsation and which is configured to increase a driving frequency of the piezoelectric element as the detected moving speed of the nozzle increases from a first detected moving speed to a second detected moving speed.

2. The medical apparatus according to claim 1, wherein the pulsation-generation control unit performs the pulsation control by increasing the driving frequency of the piezoelectric element when the moving speed of the nozzle increases or reducing the driving frequency of the piezoelectric element when the moving speed of the nozzle decreases.

3. The medical apparatus according to claim 1, wherein the pulsation-generation control unit is a unit configured to change, according to the driving frequency, a supply flow rate of the liquid supplied to the liquid chamber by the liquid supply unit.

4. The medical apparatus according to claim 3, wherein the pulsation-generation control unit increases the supply flow rate as the driving frequency is higher.

5. The medical apparatus according to claim 4, wherein, when the driving frequency corresponding to the moving speed of the nozzle exceeds a predetermined upper limit frequency, the pulsation-generation control unit retains the driving frequency at the upper limit frequency.

6. The medical apparatus according to claim 5, further comprising an informing unit configured to inform, when the driving frequency is retained at the upper limit frequency, that the driving frequency is retained.

7. The medical apparatus according to claim 4, wherein, when the supply flow rate reaches an upper limit supply flow rate, which is an upper limit value of the supply flow rate, the pulsation-generation control unit retains the driving frequency at a driving frequency set when the supply flow rate reaches the upper limit supply flow rate.

8. The medical apparatus according to claim 6, wherein the informing unit is further configured to inform, when the supply flow rate reaches the upper limit supply flow rate, that the driving frequency is retained.

9. The medical apparatus according to claim 3, wherein the pulsation-generation control unit controls the liquid supply unit to set the supply flow rate to a flow rate larger than a flow rate obtained by multiplying a decrease amount of the capacity of the liquid chamber reduced by the pulsation generating unit with the driving frequency.

10. The medical apparatus according to claim 1, further comprising:
    a liquid ejecting unit including the liquid ejection pipe erected therefrom and the liquid chamber formed on an inside thereof;
    a photographing unit configured to photograph the liquid ejecting unit from at least two directions at a predetermined time interval; and
    a mark member attached to a predetermined position of at least one of the liquid ejecting unit and the liquid ejection pipe, wherein
    the moving-speed detecting unit detects the moving speed of the nozzle by detecting a position of the mark member out of an image photographed by the photographing unit.

11. The medical apparatus according to claim 10, wherein the mark member is attached to a plurality of places of at least one of the liquid ejecting unit and the liquid ejection pipe, and
    the moving-speed detecting unit detects a direction of the nozzle on the basis of positions of a plurality of the mark members and detects moving speed of the nozzle taking into account the direction of the nozzle as well.

12. The medical apparatus according to claim 10, wherein the mark member is a member stuck to at least one of the liquid ejecting unit and the liquid ejection pipe.

13. The medical apparatus according to claim 1, wherein the moving-speed detecting unit is configured to detect the moving speed of the nozzle along three axes which are orthogonal to one another.

* * * * *